United States Patent [19]

Matsuura et al.

[11] Patent Number: 5,579,362
[45] Date of Patent: Nov. 26, 1996

[54] METHOD OF AND APPARATUS FOR THE QUANTITATIVE MEASUREMENT OF PAINT COATING

[75] Inventors: Naoki Matsuura; Seiya Shibata; Tatsuo Fukuzaki, all of Takatsuki; Akira Tanaka, Sakai; Shigeo Fukuda, Kurashiki; Hiroki Nishiyama, Funahashi; Mitsuru Tanaka, Osaka, all of Japan

[73] Assignees: Rigaku Industrial Corp.; Igeta Steel Sheet Co., Ltd., both of Osaka; Kawatetsu Galvanizing Co., Ltd.; Taiyo Steel Co., Ltd., both of Tokyo; Yodogawa Steel Works, Ltd., Osaka, all of Japan

[21] Appl. No.: 576,853

[22] Filed: Dec. 22, 1995

Related U.S. Application Data

[63] Continuation of Ser. No. 255,908, Jun. 8, 1994, abandoned, which is a continuation of Ser. No. 159,712, Dec. 1, 1993, abandoned, which is a continuation of Ser. No. 890,269, May 29, 1992, abandoned.

[30] Foreign Application Priority Data

Sep. 19, 1991 [JP] Japan ..................... 3-270044
Dec. 27, 1991 [JP] Japan ..................... 3-358717

[51] Int. Cl.⁶ ...................................... G01B 15/02
[52] U.S. Cl. ............................... 378/59; 378/90
[58] Field of Search ..................... 378/50, 89, 90

[56] References Cited

U.S. PATENT DOCUMENTS 5,029,337  7/1991  MacKenzie et al. ............... 378/50

FOREIGN PATENT DOCUMENTS

| 206735 | 12/1986 | European Pat. Off. |
| 63-19004 | 4/1988 | Japan. |
| 64-41810 | 2/1989 | Japan. |
| 2040037 | 8/1980 | United Kingdom. |

OTHER PUBLICATIONS

Plating Journal vol. 60, No. 2, Feb. 1973 (USA), Ogburn F; Smit J., "Fluorescent X-Ray Methods For The Measurement Of Coating Thickness", pp. 149–152.

*Primary Examiner*—Craig E. Church
*Attorney, Agent, or Firm*—Birch, Stewart, Kolasch & Birch, LLP

[57] ABSTRACT

An apparatus for and a method of measuring at least one painted layer formed on a sample to be analyzed, which sample may be, for example, a galvanized steel including a substrate having the painted layer formed thereon with or without an intervention of a primer coated layer. In the practice of the invention, radiation is directed onto a surface of the painted layer so as to excite the sample. The intensity of resultant Compton scattering rays, the intensity of resultant fluorescent X-rays emitted from zinc contained in a plated zinc and the intensity of resultant fluorescent X-rays emitted from strontium contained in the primer coated layer are measured, and also the absorption of the fluorescent X-rays are taken into consideration, to provide a basis for calculation of the amount of paint coating forming the painted layer. In this way, the amount of primer and paint material both applied to the galvanized steel can be easily measured on a non-destructive basis.

11 Claims, 8 Drawing Sheets

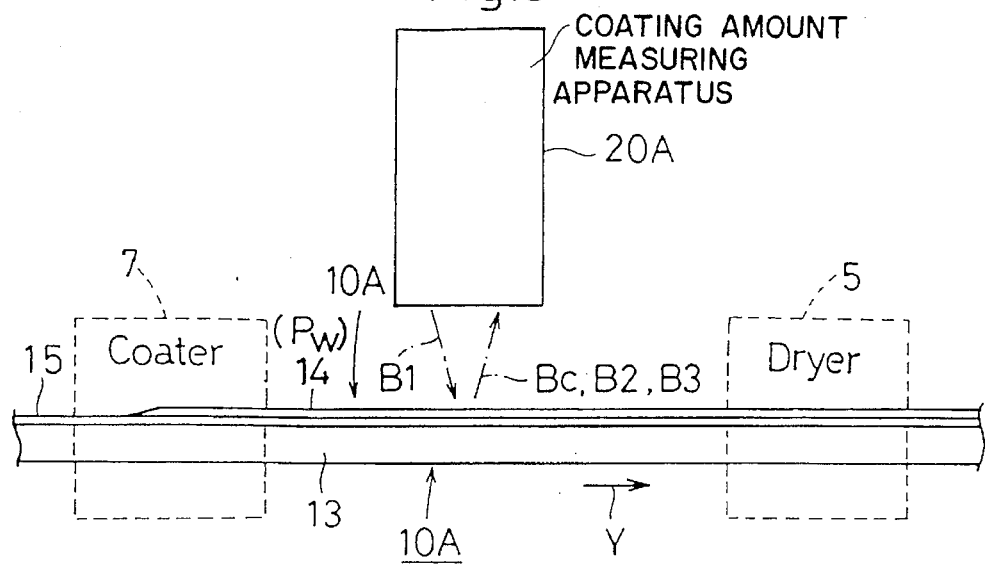
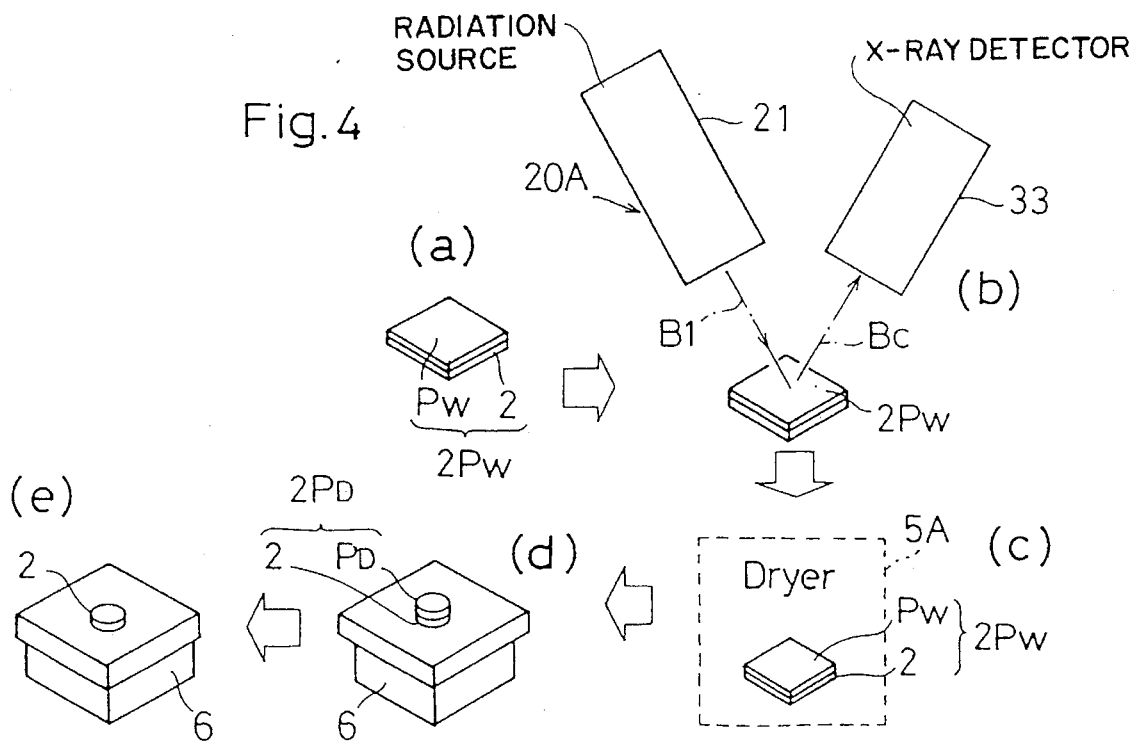

METHOD OF AND APPARATUS FOR THE QUANTITATIVE MEASUREMENT OF PAINT COATING

This application is a continuation of application Ser. No. 08/255,908 filed on Jun. 8, 1994, which is a continuation of application Ser. No. 08/159,712 filed on Dec. 1, 1993, which is a continuation of application Ser. No. 07/890,269 filed on May 29, 1992, all now abandoned.

BACKGROUND OF THE INVENTION

1. Field of the Invention

The present invention relates to a method of and an apparatus for measuring the amount of paint coating used to form one or a plurality of coated layers on a substrate such as a galvanized steel.

2. Description of the Prior Art

In general, the composition of elements forming a coating on a substrate such as, for example, at least one painted layer, is kept confidential as a know-how technology. Accordingly, an attempt has hitherto been made to measure the amount of the coating, that is, the painted layer, by irradiating a sample having a painted layer formed on a substrate and then measuring the intensity of Compton scattering rays produced from the sample, that is, radiation scattered from the sample under the well-known Compton effect. Examples of this attempt are disclosed in the Japanese Patent Publication No. Sho-63-19004 and the Japanese Laid-open Patent Publication No. Sho-64-41810.

However, since the Compton scattering rays may generate not only from the painted layers, but also from the substrate, the intensity of the Compton scattering rays as measured tends to decrease, as shown in FIG. 12(a), if even though the amount of paint coating forming the painted layer remains the same the amount of plated zinc forming a part of the substrate is large. Also, the intensity of the Compton scattering rays may differ depending on the type of material used for the plating as shown in FIG. 12(b) even though the amount of the plating material remains the same. Because of the reason mentioned above, the prior art measuring method such as disclosed in any one of the Japanese patents referred to above has managed to measure the amount of paint coating forming the painted layer with respect to the background component generating from the substrate.

However, even though the material for (or the type of) the substrate remains the same, the composition thereof, that is, the content of elements forming the substrate, may vary depending on the lot of products. In particular, in the case of the substrate comprising a galvanized steel, it is well recognized as being extremely difficult to avoid a varying thickness of a galvanized layer from one steel to another or from one lot of galvanized steel to another, resulting in an uneven amount of zinc coating.

Accordingly, the measurement of the amount of the paint coating with the use of a calibration curve appropriate to the material (type) of the substrate and/or the predetermined amount of coating of plating material (which amount is different from the actual amount of coating of plating material) often results in a measurement error due to a variation in content of the elements referred to above and/or amount of coating of the plating material.

In order to eliminate the problems discussed above, a measurement method can be contemplated which comprises irradiating a selected region of a green substrate (i.e., a substrate before a paint is applied thereto), determining a background component beforehand in reference to fluorescent X-rays produced from the green substrate, irradiating again the predetermined region of the painted substrate, that is, the substrate which has been painted, determining the intensity of Compton scattering rays produced from the painted substrate and calculating the amount of paint coating forming the paint layer with the use of the measured intensity of the Compton scattering rays and the measured background component.

According to this contemplated method, the irradiation to the predetermined region of the substrate has to be carried out twice, that is, before and after the paint application. Therefore, not only is this indeed complicated and time-consuming, but also an exact alignment of the predetermined region of the substrate before and after the paint application with the direction of irradiation is extremely difficult to achieve, and therefore, a measurement error is inevitable to a certain extent.

Specifically, where the sample to be analyzed is moving on a production line, the measurement system is required to track the sample to be analyzed. In such case, a change in speed of movement of the sample to be analyzed is apt to result in an error in measurement.

In view of the foregoing, the last-mentioned Japanese publication, that is, the Japanese Laid-open Patent Publication No. Sho-64-41810, discloses a method which comprises irradiating primary X-rays to a surface of a painted layer on a sample to be analyzed, simultaneously measuring the intensity of the Compton scattering rays and the fluorescent X-rays produced from a substrate (a plated layer) and calculating the amount of paint coating forming the painted layer on the substrate in dependence on the respective measured intensities of the radiation. However, while the fluorescent X-rays scattering from the substrate are largely absorbed by the painted layer, the above mentioned prior art has; failed to take into consideration the amount of the fluorescent X-rays absorbed by the painted layer. Because of this, information concerning the substrate, that is, the accuracy of measurement of the amount of plating material on the substrate, is extremely inaccurate and, consequently, no improvement can be found in measurement accuracy as compared with the measurement of the amount of paint coating with the use of the calibration curve appropriate to the predetermined amount of coating of plating material.

Apart from the foregoing discussion of the prior art, in the case where a painting material is applied to a plated steel, it is a general practice to apply the painting material over an outer surface of a primer. In such a case, given an amount of coating of the primer, it is possible to determine the amount of coating of the painting material over the primer by subtracting the amount of coating of the primer from the total amount of coatings including the primer and the painting material. However, the amount of coating of the primer inevitably varies from one galvanized steel to another and, on the other hand, the intensity of the Compton scattering rays scattering from the primer is, as shown in FIG. 12(c), higher than the intensity of the Compton scattering rays, scattering from the painted layer and, therefore, an error in measurement of the amount of coating of the primer coated is cumulative to an error in calculating the amount of coating of the painting material used to form the painted layer.

SUMMARY OF THE INVENTION

The present invention has, accordingly, been devised to substantially eliminate the problems discussed above and has for its essential object to provide a method of and an apparatus for measuring the amount of a painting material coated on a substrate to form painted layers, said method and said apparatus being capable of accomplishing the measurement easily and accurately regardless of the type of and material for one or both of the substrate and a plating material and also regardless of the content of elements in the substrate and/or the amount of the plating material plated to the substrate.

It is an another important object of the present invention to provide a method of and an apparatus for easily and accurately measuring the amount of a painting material coated on a substrate to form painted layers, said method and said apparatus being capable of accomplishing the measurement of the amount of a painting material forming one of the painted layers most remote from the substrate, easily and accurately regardless of a variation in an amount of the painting material forming any one of the remaining painted layer or layers.

In order to accomplish the first mentioned object of the present invention, radiation is directed onto a surface of a sample comprising the substrate having the painted layer thereon so that the intensity of Compton scattering rays emitted from the sample as a result of the irradiation and, also, a physical quantity of the substrate of the sample, which quantity corresponds to the intensity of the Compton scattering rays emitted from the substrate and forming a background component can be measured. The physical quantity referred to above may be, for example, the intensity of fluorescent X-rays or that of back scattering of β-rays, each ray being emitted from the substrate. The amount of coating of the painting material is then calculated in reference to the intensity of the Compton scattering rays and the physical quantity of the background component. At the time of calculation, the amount of the physical quantity corresponding to the background component is corrected by the amount of absorption which has been absorbed by the painted layers during the calculation of the amount of coating of the painting material.

In the practice of the present invention, since the Compton scattering rays emitted from the sample as a result of the irradiation and, also, a physical quantity of the sample corresponding to the intensity of the Compton scattering rays forming a background component are measured, and the physical quantity measured at the same position of the sample as that from which the Compton scattering rays have been emitted can be measured, it is possible to accomplish a correction of the background component. Accordingly, regardless of a change in type of material for the substrate and/or type of plating material plated to the substrate and, also, regardless of a change in content of elements forming the substrate and amount of coating of the plating material, the amount of coating of the painting material forming the painted layer can easily be measured. In particular, since the amount of the physical quantity which has been absorbed by the painted layer is used for correction during the determination of the amount of coating of the painting material, information of the substrate such as the amount of coating of the plating material can be accurately grasped, resulting in a sufficiently accurate measurement of the amount of coating of the painting material. In addition, since there is no need to align regions to be irradiated by the radiations and also to track the sample, the measurement can easily be accomplished.

Where the painting material is applied to the substrate to form painted layers, it is preferred that the physical quantity of some of the painted layers, which are closest to the substrate and except for an outermost paint layer, which quantity corresponds to the intensity of the Compton scattering rays forming a background component is measured so that the amount of coating of the painting material forming the outermost painted layer can be measured with due regard paid to the measured physical quantity.

In order to accomplish the above discussed second object of the present invention, a surface of a sample comprising the substrate having the outer and inner painted layer thereon is irradiated, and, the intensity of Compton scattering rays emitted from the sample as a result of the irradiation, a first physical quantity, for example, first fluorescent X-rays which correspond to the intensity of the Compton scattering rays emitted from the substrate of the sample and forming a first background component, and a second physical quantity, for example, second fluorescent X-rays which correspond to the intensity of the Compton scattering rays emitted from the inner painted layer of the sample and forming a second background component are measured. The amount of coating of the painting material is then calculated in reference to the intensity of the Compton scattering rays and the respective first and second physical quantities.

In the practice of the present invention, the Compton scattering rays emitted from the sample as a result of the irradiation, the first physical quantity of the first fluorescent X-rays emitted from the substrate of the sample, and the second physical quantity of the second fluorescent X-rays emitted from the inner painted layer of the sample are measured. In other words, the intensity of Compton scattering rays emitted from the sample as a result of the irradiation, the first physical quantity which correspond to the intensity of the Compton scattering rays emitted from the substrate of the sample and forming a first background component, and the second physical quantity which correspond to the intensity of the Compton scattering rays emitted from the inner painted layer of the sample and forming a second background component are measured. Therefore, the first and second physical quantities can be measured at the same position of the sample as that from which the Compton scattering rays have been emitted and, accordingly, regardless of a change in type of material for the substrate and/or type of plating material plated to the substrate, also regardless of a change in content of elements forming the substrate and amount of coating of the plating material, and regardless of a variation in an amount of coating of the painting material forming the inner painted layer, the amount of coating of the painting material forming the outer painted layer can easily be measured. In addition, since there is no need to align regions to be irradiated or to track the sample, the measurement can easily be accomplished.

Where the substrate is a plated steel, the intensity of the fluorescent X-rays emitted from the substrate may be represented by the intensity of fluorescent X-rays emitted from a plated layer.

Also, even where the sample comprises the substrate continued in a moving direction and having a wet inner painted layer and the outer painted layer overlaying the wet inner painted layer, the measurement of the amount of the painting material deposited on the substrate to form the outer painted layer is possible. In this case, the wet painted layer contains a volatile component and the volatile component emits Compton scattering rays when excited by the irradiation. Also, the amount of the volatile component evaporated varies with a passage of time. Because of this, the use is preferred of a calibration curve or a constant $\alpha$ of the calibration curve, which is determined in the following manner in calculating the amount of coating of the painting material used to form the outer painted layer.

In other words, according to a preferred embodiment of determining of the calibration curve, a weight of a specimen cut from the substrate before the painting material is applied is first measured and, thereafter a painting material of a composition identical with that of the painting material used to form the outer painted layer of the continuous substrate is applied to the cut piece to provide a standard sample. Then the weight of the standard sample in a wet condition is measured while, at the same time, the standard sample is irradiated so that the intensity of Compton scattering rays emitted from the standard sample can be measured. Subsequently, the amount of coating of the painting material on the standard sample is determined in reference to the measured weight of the standard sample and that measured in the wet condition during the irradiation The calibration curve is finally determined on the basis of the amount of coating of the painting material on the standard sample and the intensity of the Compton scattering rays emitted from the sample. The calculation of the amount of coating of the painting material forming the outer painted layer on the continuous substrate is carried out with the use of the calibration curve so determined.

According to another preferred embodiment of determining the calibration curve, a change in amount of a volatile component of the painting material forming the outer painted layer with a passage of time is first determined and, then, a painting material of a composition identical with that of the painting material used to form the outer painted layer is applied to a substrate comprising a cut piece to thereby provide a standard sample. Thereafter, the standard sample is irradiated so as to measure an intensity of Compton scattering rays emitted from the standard sample in a wet condition. Subsequently, the amount of the volatile component which has been evaporated is then determined in reference to the length of time passed immediately after the application of the painting material to the cut piece and by the time the intensity of the Compton scattering rays emitted from the standard sample has been measured and also in reference to the change in amount of the volatile component with a passage of time. The amount of coating of the painting material on the standard sample at the time of the irradiation is thereafter determined by subtracting the amount of the volatile component evaporated from the amount of coating of the painting material immediately after the painting material has been applied to the specimen to form the standard sample so that the calibration curve can be determined on the basis of the amount of coating of the painting material on the standard sample and the intensity of the Compton scattering rays emitted from the sample. Thus, using this calibration curve, the amount of coating of the painting material forming the outer painted layer on the continuous substrate can be calculated.

According to a further preferred embodiment of determining the calibration curve, the first constant α1 of calibration curve representative of a volatile component of the painting material obtained by measuring the volatile component contained in the painting material forming the outer painted layer and the second constant α2 of calibration curve representative of a non-volatile component of the painting material obtained by measuring the non-volatile component contained in the painting material forming the outer painted layer, are determined. A constant α of calibration curve is determined on the basis of the first and second constants α1 and α2 and, also, on the basis of a proportion of the non-volatile component remaining in the painting material forming the outer painted layer. Using this constant α of calibration curve, the amount of coating of the painting material forming the outer painted layer on the substrate can be calculated.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined solely by the appended claims. In the accompanying drawings, like reference numerals are used to denote like parts throughout the several views, and:

FIG. 3 is a schematic diagram showing how the intensity of Compton scattering rays is measured while a sample to be analyzed is moving on a coating line;

FIG. 4 is a diagram showing the sequence of determination of a calibration curve using drawdown specimens;

DETAILED DESCRIPTION OF THE PREFERRED EMBODIMENTS

Figure 1:
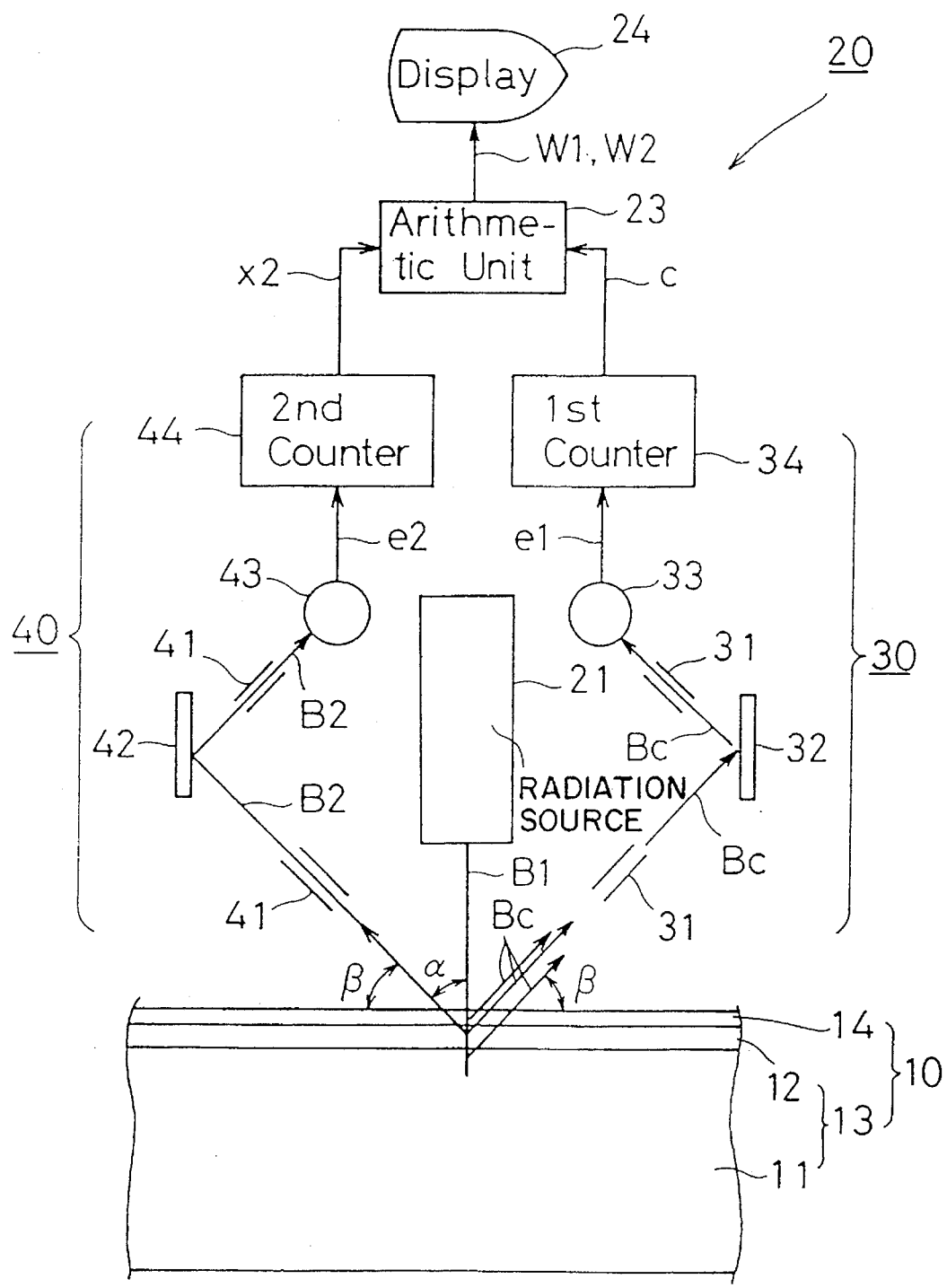
FIG. 1 is a schematic diagram showing an apparatus for measuring the amount of coating according to a first preferred embodiment of the present invention.

Referring first to FIG. 1 pertaining to a first preferred embodiment of the present invention, a sample 10 to be analyzed is shown to comprise a substrate 13 including a steel 11 and a galvanized layer 12 of zinc, and a painted layer 14 overlaying the galvanized layer 12. This sample 10 is shown to be continuously moved in one direction as, for example, transported by means of a coil drive. At one station along the path of movement of the sample 10, an apparatus 20 for the measurement of the amount of coating of the paint layer 14 on the substrate 13 is installed.

As shown therein, the measurement apparatus 20 comprises a source 21 of radiation, first and second analyzers 30 and 40, an arithmetic unit 23 and a display unit 24. The source 21 of radiation is used to apply a beam of radiation B1 onto a surface of the painted layer 14 of the sample 10 to be analyzed and may comprise an X-ray tube or a radioactive element such as, for example, americium.

The first analyzer 30 includes an optical collimating system 31, a first spectroanalyzing crystal 32, a first detector 33 and a first counting circuit 34 and is operable to measure the intensity of Compton scattering rays Bc scattering from the sample 10 which has been applied with radiations B1 emitted from the radiation source 21. The first spectroanalyzing crystal 32 is used to diffract the Compton scattering rays Bc, scattered from the sample 10, at a predetermined angle of diffraction so that the Compton scattering rays Bc can enter the first detector 33. This first detector 33 detects the Compton scattering rays Bc incident thereupon to generate a detected output e1 to the first counting circuit 34. The first counting circuit 34 then counts the detected output e1 and subsequently outputs to the arithmetic unit 23 a first measurement signal c indicative of the intensity of the Compton scattering rays Bc.

The second analyzer 40 includes an optical collimating system 41, a second spectroanalyzing crystal 42, a second detector 43 and a second counting circuit 44 and is operable to measure a physical amount which corresponds to a background component of the Compton scattering rays Bc, scattering from the substrate 13 of the sample 10, which has been applied with radiation B1 emitted from the radiation source 21. In the illustrated embodiment, the second analyzer 40 is used to measure the intensity of fluorescent X-rays B2 emitted by zinc.

The sample 10 is, when applied with the radiation B1, excited to emit the fluorescent X-rays. The second spectroanalyzing crystal 42 serves to diffract at a predetermined angle of diffraction a component of the fluorescent X-rays which is peculiar to the zinc, that is, the fluorescent X-ray B2, so that the fluorescent X-ray B2 can enter the second detector 43. This second detector 43 detects the incident fluorescent X-rays B2 peculiar to the zinc to generate a detected output e2 to the second counting circuit 44. The second counting circuit 44 then counts the detected output e2 and subsequently outputs to the arithmetic unit 23 a second measurement signal x2 indicative of the intensity of the fluorescent X-rays B2 peculiar to the zinc.

The arithmetic unit 23 upon receipt of the first and second measurement signals c and x2 calculates the amount of coating of the painted layer 14 in dependence on both of the intensity of the Compton scattering rays Bc and the intensity (physical quantity) of the fluorescent X-rays B2.

Hereinafter, a method of calculating the amount of coating of the painted layer 14 performed by the arithmetic unit 23 will be discussed.

The Compton scattering rays Bc emanate from any of the painted layer 14, the galvanized layer 12 and the steel 11 and the intensity thereof is expressed by the following equation (1):

$$I_C = I_C^P + I_C^{Zn} + I_C^{Fe} \quad (1)$$

wherein:

$I_C$: The intensity of the Compton scattering rays actually measured.

$I_C^P$: The intensity of the Compton scattering rays scattering from the painted layer 14.

$I_C^{Zn}$: The intensity of the Compton scattering rays scattering from the galvanized layer 12 and forming a background component.

$I_C^{Fe}$: The intensity of the Compton scattering rays, scattering from the steel 11 and forming a background component.

On the other hand, the intensities $I_C$, $I_C$ and $I_C$ from the painted layer 14, the galvanized layer 12 and the steel 11, respectively, can be expressed by the following equations (2), (3) and (4).

$$I_C^P = k \frac{\Sigma Z_i \cdot G_i(v) \cdot w_i/A_i}{\Sigma\{(\mu/\rho)_i^{1st} \cdot w_i/\sin\alpha + (\mu/\rho)_i^C \cdot w_i/\sin\beta\}} \times$$
$$[1 - \exp\{-\Sigma(\mu/\rho)_i^{1st} w_i/\sin\alpha + (\mu/\rho)_i^C w_i/\sin\beta\}W_P\}] \quad (2)$$

wherein:

$Z_i G_i(v)$: The Compton scattering power of an i element contained in the painted layer 14.

$Z_i$: The atomic number of the i element contained in the painted layer 14.

$A_i$: The atomic weight (mass) of the i element contained in the painted layer 14.

$w_i$: The weight ratio of the i element contained in the painted layer 14 (where $\Sigma w_i = 1$).

$(\mu/\rho)_i^j$: The coefficient of mass absorption of the i element with respect to a j spectrum. (1st represents primary X-rays and C represents the Compton scattering rays.)

$\alpha$: The angle of incidence of the radiations B1.

$\beta$: The angle of reflection of the radiations B2.

$W_P$: The amount of coating of a paint material 14.

k: An apparatus constant peculiar to optical systems and associated component parts.

exp: An exponential function $$I_C^{Zn} = k \frac{Z_{Zn} G_{Zn}(v) \cdot 1/A_{Zn}}{(\mu/\rho)_{Zn}^{1st}/\sin\alpha + (\mu/\rho)_{Zn}^C/\sin\beta} \times$$
$$[1 - \exp\{-\{(\mu/\rho)_{Zn}^{1st}/\sin\alpha + (\mu/\rho)_{Zn}^C/\sin\beta\}W_{Zn}\}] \times$$
$$\exp\{-\Sigma(\mu/\rho)_i^{1st} w_i/\sin\alpha + (\mu/\rho)_i^C w_i/\sin\beta\}W_P\} \quad (3)$$

wherein $W_{Zn}$ represents the amount of coating of zinc forming the galvanized layer 12.

$$I_C^{Fe} = k \frac{Z_{Fe} G_{Fe}(v) \cdot 1/A_{Fe}}{(\mu/\rho)_{Fe}^{1st}/\sin\alpha + (\mu/\rho)_{Fe}^C/\sin\beta} \times$$
$$[1 - \exp\{-\{(\mu/\rho)_i^{1st}/\sin\alpha + (\mu/\rho)_{Fe}^C/\sin\beta\}W_{Fe}\}] \times$$
$$\exp\{-\Sigma(\mu/\rho)_i^{1st} w_i/\sin\alpha + (\mu/\rho)_i^C w_i/\sin\beta\}W_P\} \times$$
$$\exp\{-\{(\mu/\rho)_{Zn}^{1st}/\sin\alpha + (\mu/\rho)_{Zn}^C/\sin\beta\}W_{Zn}\} \quad (4)$$

In the equation (4) above, since the thickness $W_{Fe}$ of the steel 11 may be considered infinity in terms of the reach of the X-rays, that is, since the intensity $I_C$ of the Compton scattering rays is constant at a saturated value regardless of the thickness $W_{Fe}$ of the steel 11, the equation (4) can be expressed as the following alternative equation (5):

$$I_C^{Fe} = k \frac{Z_{Fe} G_{Fe}(v) \cdot 1/A_{Fe}}{(\mu/\rho)_{Fe}^{1st}/\sin\alpha + (\mu/\rho)_{Fe}^C/\sin\beta} \times$$
$$\exp\{-\Sigma(\mu/\rho)_i^{1st} w_i/\sin\alpha + (\mu/\rho)_i^C w_i/\sin\beta\}W_P\} \times$$
$$\exp\{-\{(\mu/\rho)_{Zn}^{1st}/\sin\alpha + (\mu/\rho)_{Zn}^C/\sin\beta\}W_{Zn}\} \quad (5)$$

In further discussion, in place of the equation (4), the equation (5) will be employed.

Considering the equations (1), (2), (3) and (5), it is clear that the intensity $I_C$ of the Compton scattering rays Bc varies not only with the amount $W_P$ of coating of the painted layer 14, but also with the amount $W_{Zn}$ of coating of the galvanized layer 12. Accordingly, as hereinbefore discussed, a correction is needed to the amount $W_{Zn}$ of the galvanized layer 12.

The relationship between the amount $W_{Zn}$ of the zinc forming the galvanized layer 12 and the intensity $I_{Zn}$ of the fluorescent X-rays B2 peculiar to the galvanized layer 12 can be expressed by the following equation (6):

$$I_{Zn} = K \frac{1}{(\mu/\rho)_{Zn}^{1st}/\sin\alpha + (\mu/\rho)_{Zn}^{Zn-k}/\sin\beta} \times \quad (6)$$

$$[1 - \exp\{-\{(\mu/\rho)_{Zn}^{1st}/\sin\alpha + (\mu/\rho)_{Zn}^{Zn-k}/\sin\beta\}W_{Zn}\}] \times$$

$$\exp\{-\Sigma\{(\mu/\rho)_k^{1st} w_k/\sin\alpha + (\mu/\rho)_k^{Zn-k} w_k/\sin\beta\}W_P\}$$

wherein:

$I_{Zn}$: The intensity of the fluorescent X-rays B2 peculiar to the zinc forming the galvanized layer 12.

$w_k$: The weight ratio of a k element contained in the painted layer 14 (where $\Sigma w_k = 1$).

K: An apparatus constant peculiar to optical systems and associated component parts.

The fluorescent X-rays B2 peculiar to the zinc forming the galvanized layer 12 are absorbed as expressed by the equation (6) above in a quantity dependent on the amount $W_P$ of coating of the painting material used to form the painted layer 14. Accordingly, the foregoing relationship between the intensity $I_{Zn}$ of the fluorescent X-rays B2 and the amount $W_{Zn}$ of the zinc forming the galvanized layer 12 is delivered with respect to the amount of the fluorescent X-rays B2 peculiar to the zinc which have been absorbed by the painted layer 14, that is, by adding an absorptive correction term.

Since the foregoing equations (1) (or the equations (2), (3) and (5)) and (6) form simultaneous equations in which the amount $W_P$ of the painting material used to form the painted layer 14 and the amount $W_{Zn}$ of coating of the zinc forming the galvanized layer 12 are unknown quantities, solving these simultaneous equations can give the amount $W_P$ of coating of the painting material forming the painted layer 14. While the simultaneous equations represent an exponential function, and since the amount $W_P$ of coating of the painting material forming the painted layer 14 is generally considered small in terms of the reach of the X-rays, that is, since the amount of the Compton scattering rays Bc unique to the painted layer 14 which have been absorbed is extremely small, the equation (1) (or the equations (2), (3) and (5)) can be simplified as the following equation (7), resulting in the determination with high accuracy of the amount $W_P$ of coating of the painting material forming the painted layer 14. A similar description may applies to the equation (6) and the equation (6) can be simplified as the following equation (8).

$$W_P = a_1 I_C + b_1 + c_1 \exp(-d_1 W_{Zn}) \quad (7)$$

$$I_{Zn} = a_2\{1 - \exp(-b_2 W_{Zn})\}\exp(-c_2 W_P) \quad (8)$$

wherein $a_1$, $a_2$, $b_1$, $b_2$, $c_1$, $c_2$ and $d_1$ represent respective constants.

As discussed hereinabove, the arithmetic unit 23 makes use of the constants $a_1$, $a_2$, $b_1$, $b_2$, $c_1$, $c_2$ and $d_1$ unique to the apparatus component parts and the painting material to respond to the measurement signals c and x2 to determine the respective amounts $W_P$ and $I_{Zn}$ of coating of the painting material forming the painted layer 14 and the zinc forming the galvanized layer 12. In determining these amounts $W_P$ and $I_{Zn}$, the arithmetic unit 23 takes into consideration the amount of the fluorescent X-rays B2 which have been absorbed by the painted layer 14 by performing an addition of the absorptive correction term, $\exp(-c_2 W_P)$.

Subsequent to the calculation of the amounts $W_P$ and $I_{Zn}$ discussed above, the arithmetic unit 23 feeds the display unit 24 with respective coating signals w1 and w2 which are subsequently displayed by the display unit 24 in the form of numeric values or bar graphs or a combination thereof which are, in any event, descriptive of the amount $W_P$ of the painting material deposited to form the painted layer 14 and the amount $I_{Zn}$ of the zinc deposited to form the galvanized layer 12. The display unit 23 referred to above may be of a type including a recorder or printer operable to provide a recording of the measured amounts $W_P$ and $I_{Zn}$.

The operation of the measuring apparatus of the above described construction will now be described.

Assuming that a beam B1 is irradiated from the source 21 of radiation towards a surface of the painted layer 14 of the sample 10 to be analyzed, the first analyzer 30 measures the intensity $I_C$ of the Compton scattering rays Bc and, at the same time, the second analyzer 40 measures the intensity $I_{Zn}$ of the fluorescent X-rays B2 peculiar to the zinc forming the galvanized layer 12. Upon receipt of the measurement signals c and x2 generated from the respective first and second counting circuits 34 and 44 of the first and second analyzers 30 and 40, the arithmetic unit 23 performs the simplified equations (7) and (8) to determine the amount $W_{Zn}$ of zinc deposited on the steel 11 to form the galvanized layer 12 and the amount $W_P$ of the painting material deposited over the galvanized layer 12 to form the painted layer 14. In this way, the correction to compensate for a change attributable to the background component of the Compton scattering rays Bc which component varies with a change in amount of the zinc is carried out.

Thus, since the compensation for the background component is carried out by simultaneously measuring the Compton scattering rays Bc and the fluorescent X-rays B2 attributable to the zinc, both scattering from the sample 10 to which the radiation B1 has been applied, the correction can be carried out with no need to track the movement of the sample 10 being moved. Accordingly, even though the amount of coating of the zinc varies from place to place on the galvanized steel having the painted layer overlaying the galvanized layer, the amount of coating of the painting material forming the painted layer 14 can easily be measured. In particular, since the amount of the fluorescent X-rays B2 peculiar to the zinc which have been absorbed by the painted layer 14 has been taken into consideration during the determination of the amount of coating of the painting material 14, information of the substrate 13 such as the amount of coating of the plated zinc can be accurately grasped, resulting in a sufficiently accurate measurement of the amount of coating of the painting material forming the painted layer 14.

Also, since use has been made of only one source 21 of radiation for the measurement of both of the amount of coating of the painting material and the amount of coating of the plated zinc, the apparatus is simple in structure and inexpensive as compared with any other apparatus which requires a measurement of the amount of coating of the plated zinc before the painted layer is formed and, also, that of the amount of coating of the painting material forming the painted layer after the paint application.

It has often been observed that, where a continuous quantitative measurement is carried out to the sample 10 to be analyzed that is moving, i.e., transported by means of a coil drive, along a prescribed coating line, the sample 10 may undergo an undulating motion. In the event that the sample 10 being moved undergoes an undulating motion, the intensity of the Compton scattering rays Bc does not vary appreciably, but the intensity of the fluorescent X-rays B2 peculiar to the plated zinc varies relatively considerably because of a variation in intensity of the radiations B1 impinging upon the sample 10 undergoing the undulating motion. Therefore, it is necessary to compensate for an error resulting from the undulating motion of the sample 10, allowing the arithmetic unit 23 to perform the following equation (9) to determine the ratio of the intensity $I_{Fe}$ of the fluorescent X-rays peculiar to iron relative to the intensity $I_{Zn}$ of the fluorescent X-rays peculiar to zinc, that is, $I_{Zn}/I_{Fe}$. It is to be noted that, since the thickness of the steel 11 can be considered to be infinity in terms of the reach of the X-rays, the ratio $I_{Zn}/I_{Fe}$ can be expressed as the equation (9) shows:

$$I_{Zn}/I_{Fe}=a_3\{1-\exp(-b_3W_{Zn})\}\exp(-c_3W_{Zn})\exp(-d_3W_P) \qquad (9)$$

Hereinafter, the measuring apparatus according to a second preferred embodiment of the present will be described with reference to FIGS. 2 and 3.

Figure 2:
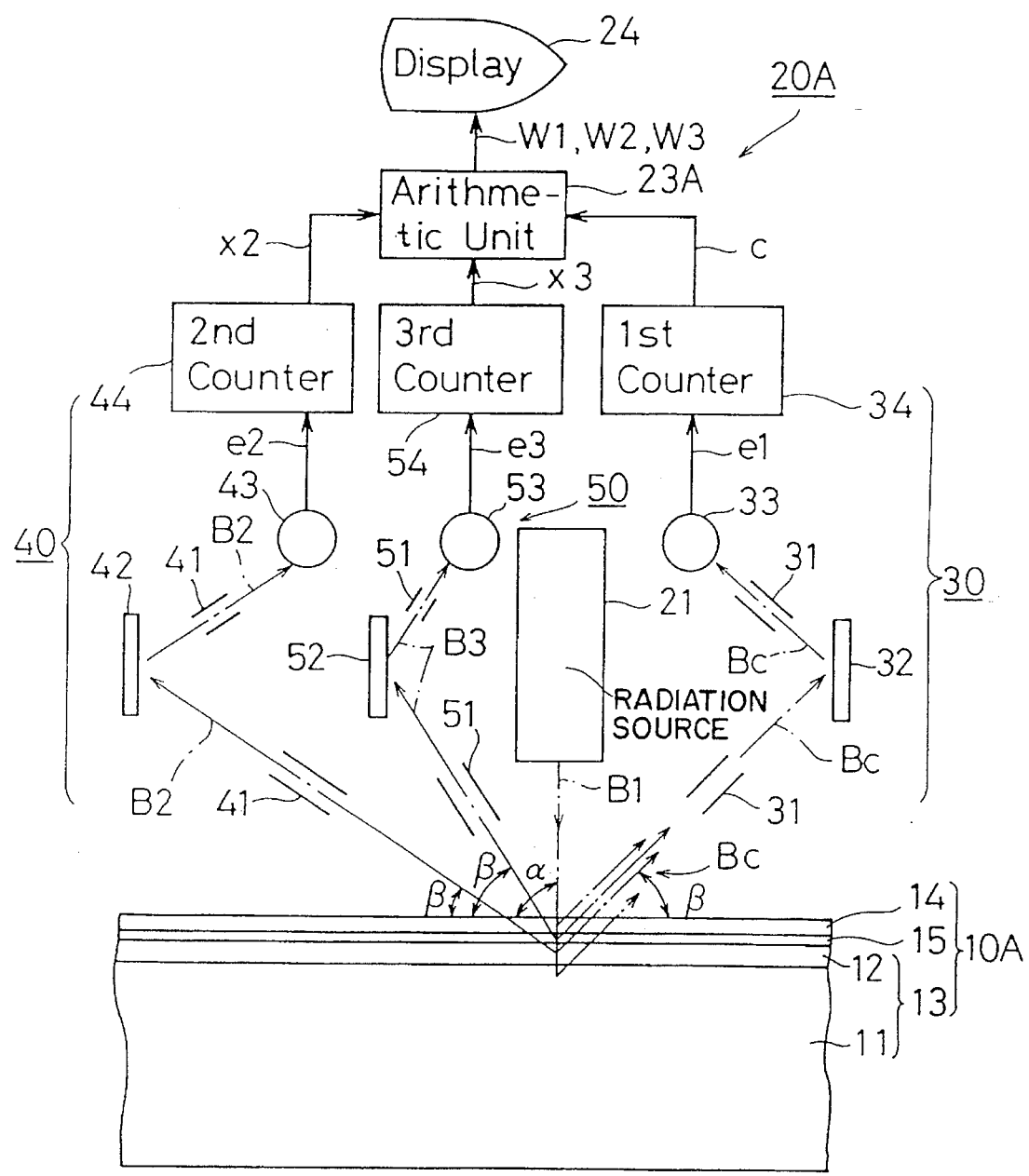
FIG. 2 is a schematic diagram showing the measuring apparatus according to a second preferred embodiment of the present invention.

As shown in FIG. 2, a sample 10A to be analyzed is shown to comprise a substrate 13 including a steel 11 and a galvanized layer 12, a lower painted layer 15 overlaying the galvanized layer 12 and an upper painted layer 14 overlaying the lower painted layer 15. It is assumed that the composition of a painting material used to form the upper painted layer 14 is unknown while the lower painted layer 15 is composed of a primer used to enhance a bondability between the galvanized layer 12 and the painting material forming the upper painted layer 14. The primer used to form the lower painted layer 15 contains strontium and chromium in a predetermined mixing ratio.

As shown in FIG. 3, the sample 10A is continuously transported by means of, for example, a coil drive in one direction shown by the arrow Y past a measuring station at which the measuring apparatus 20A is installed. Positioned upstream and downstream of the measuring station with respect to the direction Y of movement of the sample 10A are a known paint applicator machine (coater) 7 and a known drying unit (dryer) 5. In this system, the sample 10A after having been applied with a primer over the substrate 13 and after the applied primer has been dried to form the lower painted layer 15 moves successively through the applicator machine 7 and then through the drying unit 5, the painting material is applied to one surface of the lower painted layer 15 opposite to the substrate 13 and is then dried to form the upper painted layer 14. The measuring apparatus 20A installed at the measuring station immediately downstream of the applicator machine 7 performs a quantitative measurement subject to the sample while the upper painted layer 14 remains in a wet condition. It is to be noted that, as the sample 10A subsequently passes through the drying unit 5, the upper painted layer 14 is cured to assume a dry condition.

The measuring apparatus 20A shown in FIG. 2 comprises a source 21 of radiation, first, second and third analyzers 30, 40 and 50, an arithmetic unit 23A and a display unit 24. The source 21 of radiation is used to apply a beam of radiation B1 onto a surface of the upper painted layer 14 of the sample 10A to be analyzed and may comprise an X-ray tube or a radioactive element such as, for example, americium.

The first analyzer 30 includes an optical collimating system 31, a first spectroanalyzing crystal 32, a first detector 33 and a first counting circuit 34 and is operable to measure the intensity of Compton scattering rays Bc scattering from the sample 10A which has been applied with radiation B1 emitted from the radiation source 21. The first spectroanalyzing crystal 32 is used to diffract the Compton scattering rays Bc, scattered from the sample 10A, at a predetermined angle of diffraction so that the Compton scattering rays Bc can enter the first detector 33. This first detector 33 detects the Compton scattering rays Bc incident thereupon to generate a detected output e1 to the first counting circuit 34. The first counting circuit 34 then counts the detected output e1 and subsequently outputs to the arithmetic unit 23 a first measurement signal c indicative of the intensity of the Compton scattering rays Bc.

The second analyzer 40 includes an optical collimating system 41, a second spectroanalyzing crystal 42, a second detector 43 and a second counting circuit 44 and is operable to measure the fluorescent X-rays B2 scattering from the substrate 13 which has been excited by the radiation B1 emitted from the radiation source 21. In the practice of the second embodiment of the present invention, the second analyzer 40 is used to measure the intensity of fluorescent X-rays B2 emitted by zinc contained in the galvanized layer 12.

The sample 10A is, when applied with the radiations B1, excited to emit the fluorescent X-rays. The second spectroanalyzing crystal 42 serves to diffract at a predetermined angle of diffraction the fluorescent X-ray B2 peculiar to the zinc so that the fluorescent X-ray B2 can enter the second detector 43. This second detector 43 detects the incident fluorescent X-rays B2 peculiar to the zinc to generate a detected output e2 to the second counting circuit 44. The second counting circuit 44 then counts the detected output e2 and subsequently outputs to the arithmetic unit 23A a second measurement signal x2 indicative of the intensity of the fluorescent X-rays B2 peculiar to the zinc.

The third analyzer 50 is similar in construction to the second analyzer 40 and includes an optical collimating system 51, a third spectroanalyzing crystal 52, a third detector 53 and a third counting circuit 54. This third analyzer 50 is operable to measure the fluorescent X-rays B3 scattering from the lower painted layer 15, that is, the primer layer, which has been excited by the radiation B1 emitted from the radiation source 21. In the practice of this second embodiment of the present invention, the third analyzer 50 is used to measure the intensity of fluorescent X-rays B3 emitted by strontium contained in the primer layer 15.

The third spectroanalyzing crystal 52 serves to diffract at a predetermined angle of diffraction the fluorescent X-ray B3 peculiar to the strontium so that the fluorescent X-ray B3 can enter the third detector 53. This third detector 53 detects the incident fluorescent X-rays B3 peculiar to the strontium to generate a detected output e3 to the third counting circuit 54. The third counting circuit 54 then counts the detected output e3 and subsequently outputs to the arithmetic unit 23A a third measurement signal x3 indicative of the intensity of the fluorescent X-rays B3 peculiar to the strontium.

The arithmetic unit 23A upon receipt of the first to third measurement signals c, x2 and x3 calculates the amount of coating of the painting material forming the top painted layer 14 in dependence on all of the intensity of the Compton scattering rays Bc and the respective intensities of the fluorescent X-rays B2 and B3.

Hereinafter, a method of calculating the amount of coating of the upper painted layer 14 performed by the arithmetic unit 23A according to the second embodiment of the present invention will be discussed.

The Compton scattering rays Bc emanate from any of the upper painted layer 14, the primer layer 15, the galvanized layer 12 and the steel 11 and the intensity thereof is expressed by the following equation (1):

$$I_C = I_C^P + I_C^{Pri} + I_C^{Zn} + I_C^{Fe} \quad (11)$$

wherein:

$I_C$: The intensity of the Compton scattering rays actually measured.

$I_C^P$: The intensity of the Compton scattering rays scattering from the top painted layer 14.

$I_C^{Pri}$: The intensity of the Compton scattering rays scattering from the lower painted layer (the primer layer) 15.

$I_C^{Zn}$: The intensity of the Compton scattering rays scattering from the galvanized layer 12.

$I_C^{Fe}$: The intensity of the Compton scattering rays scattering from the steel 11.

On the other hand, the intensities $I_C$, $I_C$, $I_C$ and $I_C$ from the top painted layer 14, the primer layer 15, the galvanized layer 12 and the steel 11, respectively, can be expressed by the following equations (12), (13), (14) and (15).

$$I_C^P = k \frac{\Sigma Z_i \cdot G_i(v) \cdot w_i/A_i}{\Sigma\{(\mu/\rho)_i^{1st} \cdot w_i/\sin\alpha + (\mu/\rho)_i^C \cdot w_i/\sin\beta\}} \times \quad (12)$$

$$[1 - \exp\{-\Sigma\{(\mu/\rho)_i^{1st} w_i/\sin\alpha + (\mu/\rho)_i^C w_i/\sin\beta\}W_P\}]$$

wherein:

$Z_iG_i(v)$: The Compton scattering power of an i element contained in the upper painted layer 14.

$Z_i$: The atomic number of the i element contained in the top painted layer 14.

$A_i$: The atomic weight (mass) of the i element contained in the upper painted layer 14.

$w_i$: The weight ratio of the i element contained in the upper painted layer 14 (where $\Sigma w_i=1$).

$(\mu/\rho)_i^m$: The coefficient of mass absorption of the i element with respect to an m spectrum. (1st represents primary X-rays and C represents the Compton scattering rays.)

$\alpha$: The angle of incidence of the radiation B1.

$\beta$: The angle of reflection of the radiation B2.

$W_P$: The amount of coating of a paint material forming the top painted layer 14.

k: An apparatus constant peculiar to optical systems and associated component parts.

$$I_C^{Pri} = k \frac{\Sigma Z_j \cdot G_j(v) \cdot w_j/A_j}{\Sigma\{(\mu/\rho)_j^{1st} \cdot w_j/\sin\alpha + (\mu/\rho)_j^C \cdot w_j/\sin\beta\}} \times \quad (13)$$

$$[1 - \exp\{-\Sigma\{(\mu/\rho)_j^{1st} w_j/\sin\alpha + (\mu/\rho)_j^C w_j/\sin\beta\}W_{Pri}\}] \times$$

$$\exp[-\Sigma\{(\mu/\rho)_i^{1st} w_i/\sin\alpha + (\mu/\rho)_i^C w_i/\sin\beta\}W_P]$$

wherein:

$Z_jG_j(v)$: The Compton scattering power of an j element contained in the primer layer 15.

$Z_j$: The atomic number of the j element contained in the primer layer 15.

$A_j$: The atomic weight (mass) of the j element contained in the primer layer 15.

$w_j$: The weight ratio of the j element contained in the primer layer 15 (where $\Sigma w_j=1$).

$(\mu/\rho)_j^n$: The coefficient of mass absorption of the j element with respect to an n spectrum. (1st represents primary X-rays and C represents the Compton scattering rays.)

$W_{Pri}$: The amount of coating of the primer forming the primer layer 15.

$$I_C^{Zn} = k \frac{Z_{Zn}G_{Zn}(v) \cdot 1/A_{Zn}}{(\mu/\rho)_{Zn}^{1st}/\sin\alpha + (\mu/\rho)_{Zn}^C/\sin\beta} \times \quad (14)$$

$$[1 - \exp\{-\{(\mu/\rho)_{Zn}^{1st}/\sin\alpha + (\mu/\rho)_{Zn}^C/\sin\beta\}W_{Zn}\}] \times$$

$$\exp[-\Sigma\{(\mu/\rho)_i^{1st} w_i/\sin\alpha + (\mu/\rho)_i^C w_i/\sin\beta\}W_P] \times$$

$$\exp[-\Sigma\{(\mu/\rho)_j^{1st} w_j/\sin\alpha + (\mu/\rho)_j^C w_j/\sin\beta\}W_{Pri}]$$

wherein $W_{Zn}$ represents the amount of coating of zinc forming the galvanized layer 12.

$$I_C^{Fe} = k \frac{Z_{Fe}G_{Fe}(v) \cdot 1/A_{Fe}}{(\mu/\rho)_{Fe}^{1st}/\sin\alpha + (\mu/\rho)_{Fe}^C/\sin\beta} \times \quad (15)$$

$$[1 - \exp\{-\{(\mu/\rho)_i^{1st}/\sin\alpha + (\mu/\rho)_{Fe}^C/\sin\beta\}W_{Fe}\}] \times$$

$$\exp[-\Sigma\{(\mu/\rho)_i^{1st} w_i/\sin\alpha + (\mu/\rho)_i^C w_i/\sin\beta\}W_P] \times$$

$$\exp[-\Sigma\{(\mu/\rho)_j^{1st} w_j/\sin\alpha + (\mu/\rho)_j^C w_j/\sin\beta\}W_{pri}] \times$$

$$\exp[-\{(\mu/\rho)_{Zn}^{1st}/\sin\alpha + (\mu/\rho)_{Zn}^C/\sin\beta\}W_{Zn}]$$

In the equation (15) above, since the thickness $W_{Fe}$ of the steel 11 may be considered infinity in terms of the reach of the X-rays, that is, since the intensity $I_C^{Fe}$ of the Compton scattering rays is constant at a saturated value regardless of the thickness $W_{Fe}$ of the steel 11, the equation (15) can be expressed as the following alternative equation (16):

$$I_C^{Fe} = k \frac{Z_{Fe}G_{Fe}(v) \cdot 1/A_{Fe}}{(\mu/\rho)_{Fe}^{1st}/\sin\alpha + (\mu/\rho)_{Fe}^C/\sin\beta} \times \quad (16)$$

$$\exp[-\Sigma\{(\mu/\rho)_i^{1st} w_i/\sin\alpha + (\mu/\rho)_i^C w_i/\sin\beta\}W_P] \times$$

$$\exp[-\Sigma\{(\mu/\rho)_j^{1st} w_j/\sin\alpha + (\mu/\rho)_j^C w_j/\sin\beta\}W_{Pri}] \times$$

$$\exp[-\{(\mu/\rho)_{Zn}^{1st}/\sin\alpha + (\mu/\rho)_{Zn}^C/\sin\beta\}W_{Zn}]$$

In further discussion, in place of the equation (15), the equation (16) will be employed.

Considering the equations (11), (12), (13), (14) and (16), it is clear that the intensity $I_C$ of the Compton scattering rays Bc varies not only with the amount $W_P$ of coating of the painting material forming the upper painted layer 14, but also with the amount $W_{Zn}$ of coating of the zinc forming the galvanized layer 12 and with the amount $W_{Pri}$ of coating of the primer forming the primer layer 15. Accordingly, as hereinbefore discussed, a correction is needed to the amount $W_{Zn}$ of the galvanized layer 12 and also to the amount $W_{Pri}$ of coating of the primer forming the primer layer 15.

The relationship between the amount $W_{Zn}$ of the zinc forming the galvanized layer 12 and the intensity $I_{Zn}$ of the fluorescent X-rays B2 peculiar to the plated zinc can be expressed by the following equation (17):

$$I_{Zn} = K_1 \frac{1}{(\mu/\rho)_{Zn}^{1st}/\sin\alpha + (\mu/\rho)_{Zn}^{Zn-k\alpha}/\sin\beta} \times \quad (17)$$

$$[1 - \exp\{-\{(\mu/\rho)_{Zn}^{1st}/\sin\alpha + (\mu/\rho)_{Zn}^{Zn-k\alpha}/\sin\beta\}W_{Zn}\}] \times$$

$$\exp[-\Sigma\{(\mu/\rho)_i^{1st} w_i/\sin\alpha + (\mu/\rho)_i^{Zn-k\alpha} w_i/\sin\beta\}W_P] \times$$

$$\exp[-\Sigma\{(\mu/\rho)_j^{1st} w_j/\sin\alpha + (\mu/\rho)_j^{Zn-k\alpha} w_j/\sin\beta\}W_{Pri}]$$

wherein:

$I_{Zn}$: The intensity of the fluorescent X-rays B2 peculiar to the zinc forming the galvanized layer 12.

$K_1$: An apparatus constant peculiar to optical systems and associated component parts.

Also, the relationship between the amount $W_{Pri}$ of coating of the primer forming the primer layer 15 and the intensity $I_{Sr}$ of the fluorescent X-rays B2 scattering from the strontium contained in the primer layer 15 can be expressed by the following equation (18):

$$I_{Sr} = K_2 \frac{1}{(\mu/\rho)_{Sr}^{1st}/\sin\alpha + (\mu/\rho)_{Sr}^{Sr-k\alpha}/\sin\beta} \times$$

$$[1 - \exp\{-\{(\mu/\rho)_j^{1st} W_j/\sin\alpha + (\mu/\rho)_j^{Sr-k\alpha} W_j/\sin\beta\}W_{Pri}\}] \times$$

$$\exp[-\Sigma\{(\mu/\rho)_i^{1st} w_i/\sin\alpha + (\mu/\rho)_i^{Sr-k\alpha} w_i/\sin\beta\}W_P]$$

wherein:

$I_{Sr}$: The intensity of the fluorescent X-rays B2 peculiar to the strontium contained in the primer layer 15.

$K_2$: An apparatus constant peculiar to optical systems and associated component parts.

Since the foregoing equations (11) (or the equations (12), (13), (14) and (16)), (17) and (18) form simultaneous equations in which the amount $W_P$ of the painting material used to form the painted layer 14, the amount $W_{Pri}$ of coating of the primer used to form the primer layer 15 and the amount $W_{Zn}$ of coating of the zinc forming the galvanized layer 12 are unknown quantities, solving these simultaneous equations can give the amount $W_P$ of coating of the painting material forming the painted layer 14.

The foregoing equations (12), (13), (14 and (16) can be rewritten as the following equations (22), (23), (24) and (26), respectively:

$$I_C^P = A_1\{1-\exp(-B_1 W_P)\} \tag{22}$$

$$I_C^{Pri} = A_2\{1-\exp(-B_2 W_{Pri})\}\exp(-B_1 W_P) \tag{23}$$

$$I_C^{Zn} = A_3\{1-\exp(-B_3 W_{Zn})\}\exp(-B_2 W_{Pri})\times\exp(-B_1 W_P) \tag{24}$$

$$I_C^{Fe} = A_4 \exp(-B_3 W_{Zn})\exp(-B_2 W_{Pri})\exp(-B_1 W_P) \tag{26}$$

wherein $A_n$ and $B_n$ (n being an integer) represent respective constants.

Also, since the amount $W_{Pri}$ of coating of the primer forming the primer layer 15 and the amount $W_P$ of coating of the painting material forming the upper painted layer 14 are generally small in terms of the reach of the X-rays, that is, since the amount of the Compton scattering rays Bc which are absorbed by any of the painted layers 14 and 15 is slight, the foregoing equations (11) (or the equations (22), (23), (24) and (26)), (17) and (18) can be simplified as shown by (31), (37) and (38) below. Even though these equations (11), (17) and (18) are so simplified as described above, a sufficiently accurate determination of the amount $W_P$ of coating of the painting material forming the top painted layer 14 is possible.

$$I_C = A_1 B_1 W_P + A_2 B_2 W_{Pri}\exp(-B_1 W_P) + \tag{31}$$

$$A_3\{1 - \exp(-B_3 W_{Zn})\}\exp(-B_2 W_{Pri})\exp(-B_1 W_P) +$$

$$A_4\exp(-B_3 W_{Zn})\exp(-B_2 W_{Pri})\exp(-B_1 W_P)$$

$$I_{Zn} = A_5\{1 - \exp(-B_5 W_{Zn})\}\exp(-C_5 W_p) \tag{37}$$

$$I_{Sr} = A_6\{1 - \exp(-B_6 W_{Pri})\}\exp(-C_6 W_p) \tag{38}$$

$$= A_6 B_6 W_{Pri}\exp(-C_6 W_p)$$

wherein $C_n$ (n being an integer) represents a constant.

As discussed hereinabove, the arithmetic unit 23A makes use of the constants $A_n$ to $C_n$ unique to the apparatus component parts, the painting material and the primer to respond to the measurement signals c, x2 and x3, which are indicative of the respective intensities $I_C$, $I_{Zn}$ and $I_{Sr}$ of the Compton scattering rays Bc, the fluorescent X-rays B2 and the fluorescent X-rays B3, to determine the respective amounts $W_P$, $I_{Zn}$ and $W_{Pri}$ of coating of the painting material forming the upper painted layer 14, the zinc forming the galvanized layer 12 and the primer forming the primer layer 15.

Subsequent to the calculation of the amounts $W_P$, $W_{Pri}$ and $I_{Zn}$ discussed above, the arithmetic unit 23A feeds the display unit 24 with respective coating signals w1, w2 and w3 which are subsequently displayed by the display unit 24 in the form of numeric values or bar graphs or a combination thereof which are, in any event, descriptive of the amount $W_P$ of the painting material deposited to form the upper painted layer 14; the amount $W_{Pri}$ of coating of the primer forming the primer layer 15 and the amount $I_{Zn}$ of the zinc coated to form the galvanized layer 12.

The operation of the measuring apparatus of the above described construction according to the second embodiment of the present invention will now be described.

Assuming that a beam of radiation B1 is emitted from the source 21 of radiation towards a surface of the top painted layer 14 of the sample 10A, the first analyzer 30 measures the intensity $I_C$ of the Compton scattering rays Bc and, at the same time, the second and third analyzer 40 and 50 measure the intensity $I_{Zn}$ of the fluorescent X-rays B2 peculiar to the zinc forming the galvanized layer 12 and the intensity $I_{Sr}$ of the fluorescent X-ray B3 peculiar to the primer forming the primer layer 15, respectively. Upon receipt of the measurement signals c, x2 and x3 generated from the respective first, second and third counting circuits 34, 44 and 54 of the first to third analyzers 30, 40 and 50, the arithmetic unit 23A performs the simplified equations (31),(37) and (38) to determine the amount $W_{Zn}$ of zinc deposited on the steel 11 to form the galvanized layer 12, the amount $W_{Pri}$ of coating of the primer forming the primer layer 15 and the amount $W_P$ of the painting material deposited over the galvanized layer 12 to form the painted layer 14. In this way, the correction to compensate for a change attributable to the background component which varies with a change in amount of any one of the primer and the zinc is carried out.

Thus, since the compensation for the background component is carried out by simultaneously measuring the Compton scattering rays Bc and the fluorescent X-rays B2 and B3 peculiar to the zinc and the primer, all scattering from the sample 10A to which the radiation B1 has been applied, the correction can be carried out with no need to track the movement of the sample 10A being moved. Accordingly, even though the amount of coating of one or both of the zinc and the primer varies from place to place on the galvanized steel having the upper painted layer overlaying the galvanized layer with the intervention of the primer layer 15, the amount of coating of the painting material forming the upper painted layer 14 can easily be measured.

Also, since use has been made of only one source 21 of radiation for the measurement of not only the respective amounts of coating of the painting material and the primer forming the associated painted layer 14 and 15, but also the amount of coating of the plated zinc, the apparatus is simple in structure and inexpensive as compared with any other apparatus which requires a measurement of the amount of coating of the plated zinc before the painted layer is formed and, also, that of the amount of coating of the primer before the primer layer is formed and that of the amount of coating of the painting material forming the painted layer after the paint application.

It is to be noted that, in describing any one of the foregoing preferred embodiments of the present invention with particular reference to FIGS. 1 and 2, respectively, reference has been made to the galvanized steel comprising the substrate 13. However, the present invention can be equally applicable to any metallic plate or a metallic article of manufacture provided that the plate or article is plated with any material. Also, even for a stainless steel having no galvanized layer thereon, the present invention can be utilized to determine the amount of coating of the painting material, because the content of elements such as, for example, chromium, iron and nickel, contained in the stainless steel can be determined by measuring fluorescent X-rays emitted therefrom when they are excited by radiation.

It is also to be noted that, although the substrate 13 has been shown and described having been formed with a single painted layer 14 such as in the first mentioned embodiment of the present invention or with double painted layers 14 and 15 such as in the second mentioned embodiment of the present invention, the measurement according to the present invention can be equally applicable to the substrate having three or more painted or coated layers formed thereon. By way of example, where the substrate has three or more painted layers, it suffices to measure the intensity of the fluorescent X-rays emitted from the painted or coated layers except the outermost layer so that, based on respective measurements of the intensities of the fluorescent X-rays scattering from these inner layers adjacent the substrate and also from the substrate, the amount of the painting or coating material used to form the outermost layer remote from the substrate can be determined in reference to the intensity of the Compton scattering rays, that is, with the intensities of the fluorescent X-rays from the two of the layers being taken into consideration.

Again, in any one of the foregoing embodiments of the present invention, the first and second physical quantities corresponding to the background component of Compton scattering rays Bc scattering from the substrate 13 or the layer or layers adjacent the substrate in the sample 10 or 10A to be analyzed have been described as measured in terms of the intensities of the respective fluorescent X-rays B2 or B3. However, in place of the fluorescent X-rays, back scattering of β rays may be measured and then corrected in a manner substantially similar to that hereinbefore described.

Referring to the equations (22) to (26), (31), (37) and (38), the constant $A_n$ (n being an integer) referred to therein is generally known as a constant of calibration curve that is fixed for each of the measuring apparatus 20A and the type of painting material employed. The constant $A_n$ of calibration curve, for example, the constant $A_1$ in the equation (31), can be determined using a plurality of standard samples in which the amount $W_P$ of coating has been known. The manner by which and how this constant $A_1$ of calibration curve is determined, that is, by which and how the calibration curve is determined, will now be discussed.

A generalized method of determining the calibration curve will first be discussed with reference to FIG. 4. Referring first to FIG. 4(a), two sample pieces 2 are prepared from the galvanized steel of a composition identical with the substrate 13 (FIG. 3) discussed hereinbefore. Each of the two sample pieces 2 are then applied with the same painting material as that used to form the upper painted layer 14 as to deposit on the substrate of the respective specimens 2, thereby to provide a respective standard sample 2Pw that has a wet painted layer Pw (similar to the upper painted layer 14) on the respective specimens 2.

Thereafter, with respect to the standard samples 2Pw, radiation B1 is applied from the measuring apparatus 20A of the construction, as shown in FIG. 4(b), to measure the intensity $I_{C2}$ (hereinafter referred to the second intensity) of the Compton scattering rays Bc scattered from each of the standard samples Pw. Subsequent to this measurement, the standard samples 2Pw are successively loaded into the drying unit 5A, shown in FIG. 4(c), to dry the respective painted layers Pw. After the drying, respective minute portions of the standard samples 2Pw, which have been applied with the radiation B1 are cut out from the associated standard samples 2Pw to provide dried standard specimens $2P_D$ each having the dry painted layer $P_D$ (corresponding to the upper painted layer 14) as shown in FIG. 4(d).

Then, the two dried standard specimens $2P_D$ are measured as to their weight with the use of a weighing device 6 as shown in FIG. 4(d). After the weighing, the dry painted layers $P_D$ are peeled off from the associated substrates by means of a chemical process and two small pieces 2 are tested to determine their weights $W_2$ as shown in FIG. 4(e).

It is to be noted that the painting material used is of a composition containing pigments (non-volatile component) and a solvent (volatile component) mixed together in a predetermined mixing ratio. Accordingly, a subtraction of the weight $W_2$ of each of the small pieces 2 from the weight $W_{2D}$ of each of the dried standard specimens $2P_D$ gives the weight $W_D$ of only the dried painted layer $P_D$ on each small piece 2. Using this weight $W_D$ of each dried painted layer $P_D$, the weight $W_w$ of the wet painted layer $P_w$ is determined by dividing the weight $W_D$ by a proportion k of the non-volatile component in the mixing ratio of the non-volatile and volatile components forming the painting material. The weight $W_w$ is then divided by the area of surface of each of the small pieces 2 to give the amount $W_{PW}$ (amount per unit area) of coating of the painting material forming the wet painted layer Pw, followed by a determination of a relationship between the amount $W_{PW}$ and the second intensity $I_{C2}$ of the Compton scattering rays Bc thereby to give the calibration curve.

Figure 5:
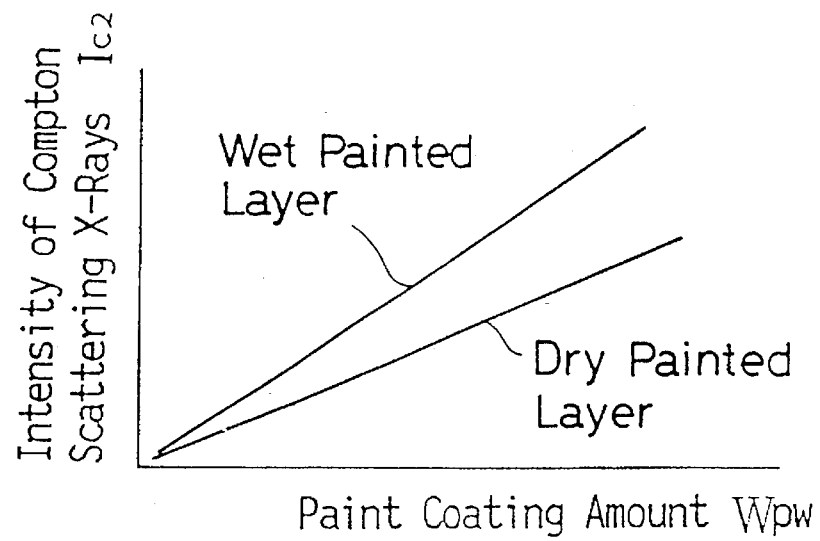
FIG. 5 is a chart showing a relationship between the intensity of Compton scattering rays and the amount of coating of any one of painted layers in wet and dry conditions, respectively.

Thus, in the practice of the present invention, the calibration curve is determined from the relationship between the amount $W_{PW}$ and the second intensity $I_{C2}$ of coating of the painting material forming the wet painted layer $W_{PW}$, but not from the relationship between the amount $W_{PW}$ of coating of the painting material forming the dry painted layer $W_{PD}$ and the second intensity $I_{C2}$. This is because, since the painting material contains the volatile component as hereinabove discussed, the respective painted layers in wet and dry conditions give a different second intensity $I_{C2}$ of the Compton scattering rays Bc even though the standard specimens 2Pw ($2P_D$) remain the same as shown in FIG. 5.

Based on the calibration curve so determined as hereinabove described, the intensity (hereinafter referred to as the first intensity) $I_C$ of the Compton scattering rays Bc measured by the measuring apparatus 20A installed at the measuring station along the production line shown in FIG. 3 and other parameters, the amount $W_{PW}$ of coating of the painting material forming the wet painted layer Pw (corresponding to the upper painted layer 14) can be determined. In this way, by the measurement of the amount $W_{PW}$ of coating of the painting material in wet condition immediately after the painting, the applicator machine 7 shown in FIG. 3 can be controlled on real-time basis to adjust the amount of coating of the painting material forming the dry painted layer.

In determining the calibration curve in the manner described above, the following care should be taken.

As can readily be understood by those skilled in the art, in the determination of the calibration curve, a length of time, say, about 1 minute, will pass inevitably subsequent to the paint application and before the standard sample 2Pw shown in FIG. 4(c) is placed at the measuring station at which the measuring apparatus 20A is installed. According to the above discussed generalized method of determination of the calibration curve, the length of time passed subsequent to the paint application shown in FIG. 4(a) and by the time the intensity of the Compton scattering rays Bc is measured as shown in FIG. 4(b) is as small as about 1 minute, and therefore, the calibration curve is formulated with no regard paid to the amount of the volatile component which has been evaporated. This is because the amount of the volatile component having been evaporated during that length of time is so small as to be negligible.

Figure 6:
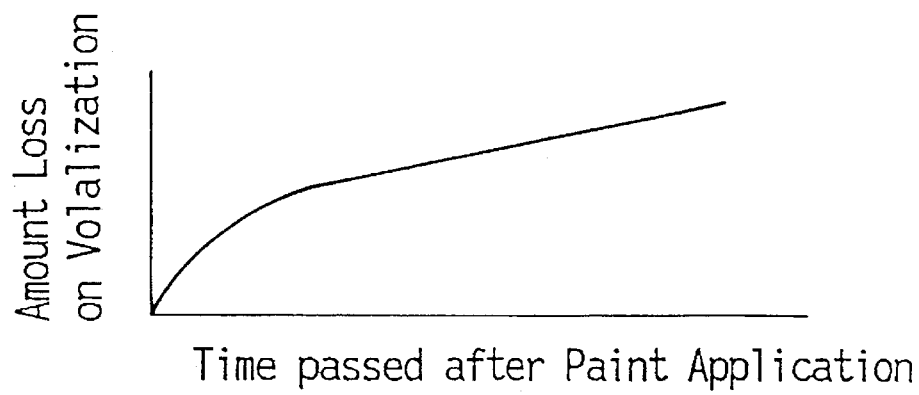
FIG. 6 is a chart showing the weight loss on volatization with a passage of time subsequent to the paint application.

However, the amount of the volatile component evaporated may be great at a time immediately after the paint application as shown in FIG. 6 and, therefore, the amount $W_{PW}$ of coating of the painting material used to form the painted layer Pw immediately after the paint application is somewhat different from that during the measurement of the second intensity $I_{C2}$ of the Compton scattering rays Bc. This difference causes an inaccurate determination of the calibration curve which eventually results in a measurement error. Consequently, the accuracy of the analysis will be lowered and, depending on the type of painting material, an error of about 3 to 4 g/m$^2$ (where the amount $W_{PW}$ is 20 g/m$^2$) will result.

In view of the foregoing, the amount Wp (or $W_{PW}$) of coating of the painting material forming the upper painted layer 14 (or Pw) is preferred to be determined by the use of the following calibration curves or by the use of the following calibration curves determined by obtaining constants of the calibration curves.

Figure 7:
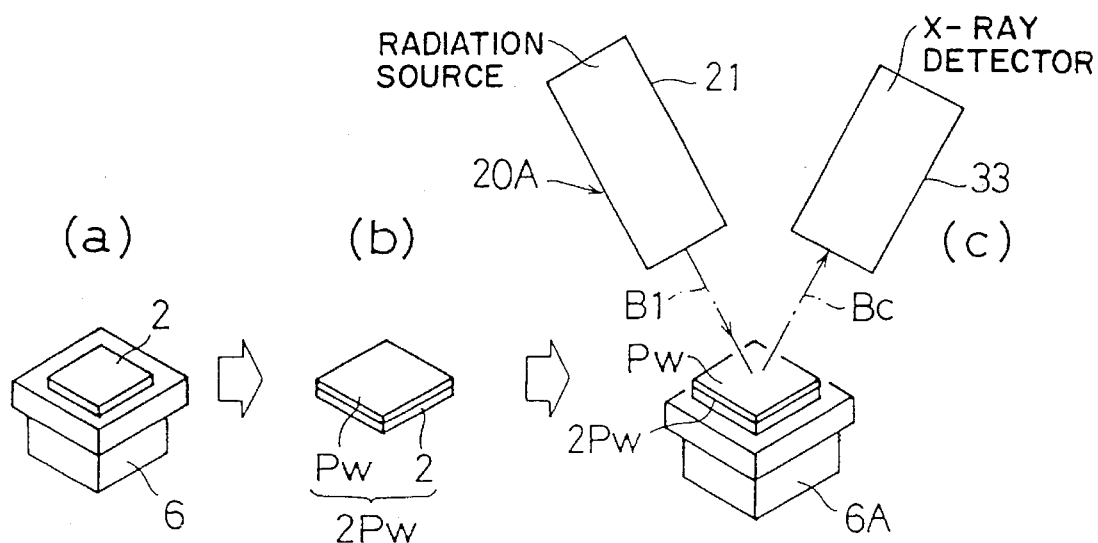
FIGS. 7(a), 7(b) and 7(c) illustrate a preferred method of determining the calibration curve.

Hereinafter, the preferred method of determination of the calibration curve will be discussed with reference to FIG. 7.

In the first place, as shown in FIG. 7(a), the substrate of the standard sample before the paint application, that is, the cut piece 2 before the paint application, is weighed by the use of a weighing device 6. Then, using a hand-held paint applicator such as, for example, a bar coater (not shown), the same paint material as that used to form the upper paint layer shown in FIG. 2 is applied to the small piece 2 to give the standard sample 2Pw having the painted layer Pw which is still in a wet condition as shown in FIG. 7(b).

After the paint application, and as shown in FIG. 7(c), the standard sample 2Pw is placed in the measuring apparatus 20A. The measuring apparatus 20A referred to includes a weighing device 6A, in addition to the source 21 of radiation and the X-ray detector 33.

After the placement of the standard sample. 2Pw in the measuring apparatus 20A, the standard sample 2Pw having the wet painted layer Pw is weighed by the use of the weighing device 6A to give a weight $W_{2W}$. Simultaneously with this weight measurement, the radiation B1 from the source 21 thereof is applied to the standard sample 2Pw. The application of the radiation B1 results in an emission of the Compton scattering rays Bc from the painted layer Pw which are subsequently incident on the X-ray detector 33. The second intensity $I_{C2}$ of the resultant Compton scattering rays Bc can be measured by a counting circuit not shown.

After the measurement of the Compton scattering rays Bc, the weight $W_2$ of the small piece 2 having no painted layers is subtracted from the weight $W_{2W}$ of the standard sample 2PW having the wet painted layer Pw to determine the weight Ws of the wet painted layer Pw. Using this weight Ww, the amount $W_{PW}$ of coating of the painting material Pw on the standard sample 2Pw is determined by dividing the weight Ww by the area of surface of the cut piece 2, followed by a determination of a relationship between the amount $W_{PW}$ and the second intensity $I_{C2}$ of the Compton scattering rays Bc thereby to give the calibration curve.

Then, with the use of the calibration curve so determined as hereinabove described, the measurement is carried out while the sample is transported along the coating line as shown in FIG. 3, to determine the amount $W_{PW}$ of the painting material forming the wet painted layer in the sample 10A to be analyzed. Thereafter, a similar measurement is carried out in a manner described in connection with the second preferred embodiment of the present invention and, therefore, the details thereof will not be reiterated for the sake of brevity.

Figure 8:
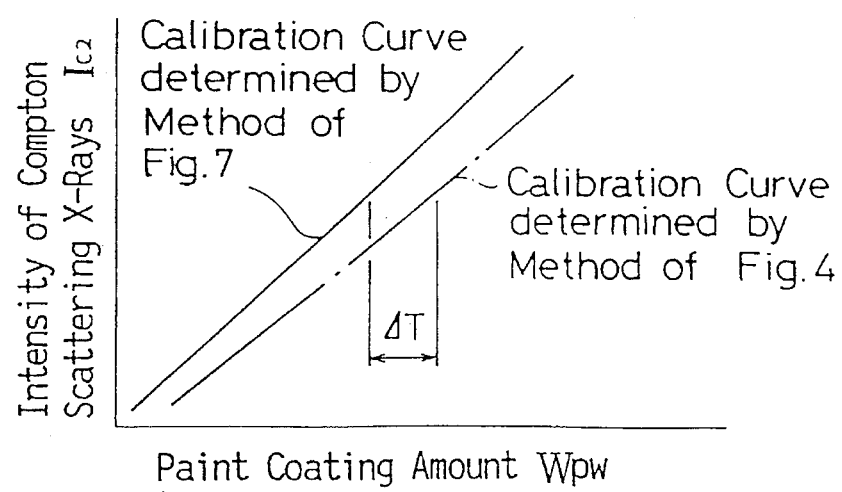
FIG. 8 is a chart showing the calibration curve determined according to the methods shown in FIG. 4 and FIG. 7, respectively.

According to the method described with reference to FIG. 7, the weighing of the standard sample 2Pw having the wet painted layer and the measurement of the second intensity $I_{C2}$ of the Compton scattering rays Bc are carried out simultaneously. Accordingly, it is possible to measure the second intensity $I_{C2}$ of the Compton scattering rays Bc which corresponds substantially exactly to the amount $W_{PW}$ of the painting material forming the wet painted layer and, therefore, with no need to effect the measurement while the sample is transported along the painting line as shown in FIG. 3, the calibration curve can be accurately determined using the standard sample 2Pw comprising the small piece 2 as the substrate. In other words, while the previously discussed generalized method has resulted in the determination of the calibration curve such as shown by a single-dotted line in FIG. 8, the above discussed preferred method can result in the accurate determination of the calibration curve, as shown by a solid line in FIG. 8, in which the rate AT (by percent) of evaporation of the volatile component from the time of paint application to the time of measurement of the Compton scattering rays Bc has been taken into consideration. Consequently, the amount $W_{PW}$ of coating of the painting material forming the painted layer in the sample 10A to be analyzed can be accurately measured.

Figure 9:
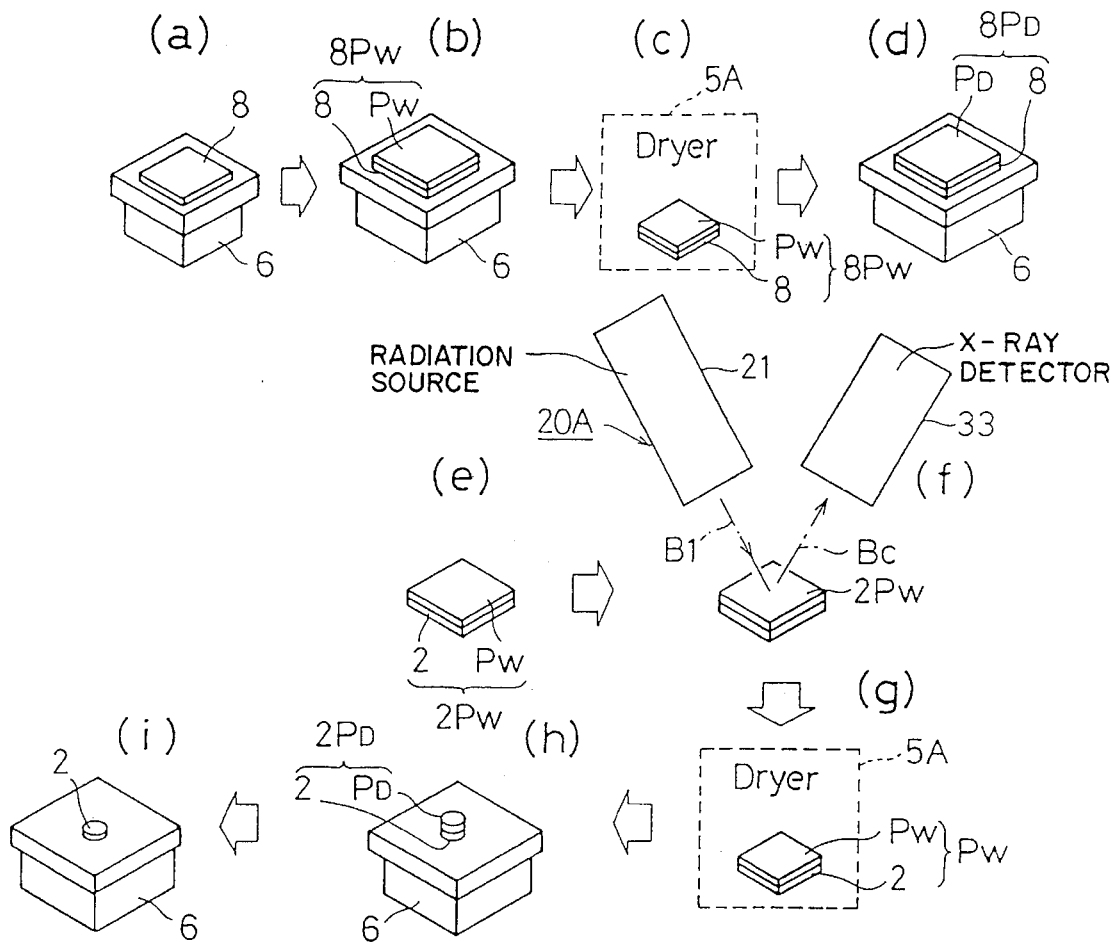
FIG. 9 is a diagram showing another preferred method of determining the calibration curve.

Another preferred method of determination of the calibration curve according to the present invention is shown in FIG. 9.

Referring first to FIG. 9(a), the weight $W_8$ of a cut piece 8 which will form a weighing sample is measured. Then, a painting material is applied to the cut piece 8 to form a wet painted layer Pw thereon, which piece 8 then serves as the weighing sample 8Pw. After this paint application, and as shown in FIG. 9(b), the weighing sample 8Pw is placed on a weighing device 6 to record a change in weight $W_{8W}$ (See FIG. 10) of the weighing sample 8Pw with a passable of time immediately subsequent from the time of paint application. The weight $W_{8W}$ can provide an indication of the amount of the volatile component evaporated during the passage of time subsequent to the paint application. After this weighing has been carried out for about two minutes, the weighing sample 8Pw is loaded into a drying unit 5A as shown in FIG. 9(c) to dry the painted layer on the weighing sample 8Pw and the dried weighing sample $8P_D$ is then placed on the weighing device 6 to measure the weight thereof as shown in FIG. 9(d).

Figure 10:
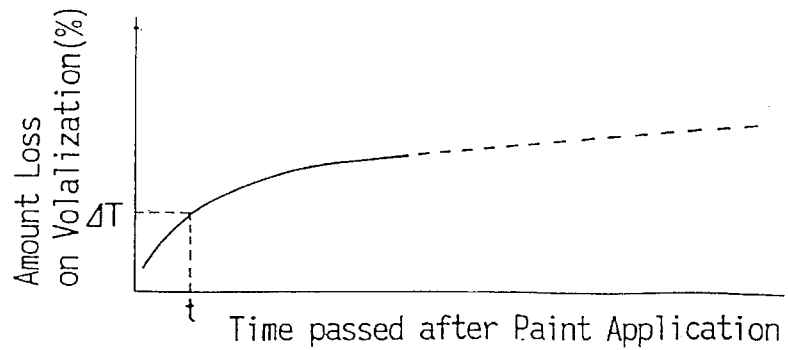
FIG. 10 is a chart showing a change in an amount of a volatile component, contained in a painting material, with a passage of time subsequent to the paint application.

Based on the measured values described with reference to FIGS. 9(d) and 9(a), the weight $W_D$ of the dry painted layer $P_D$ is determined in the manner as described with reference to FIG. 4, and based on this weight $W_D$ and the proportion of the volatile component evaporated, the weight Ww of the painted layer Pw immediately after the paint application, is determined. On the other hand, since the amount of the volatile component evaporated is known from the continuous weighing carried out in the manner described with reference to FIG. 9(b), the ratio of the amount of the volatile component relative to the weight Ww of the painted layer Pw immediately after the paint application, that is, the rate ΔT (by percent) of evaporation of the volatile component, can be determined. In this way, a change in rate ΔT of evaporation of the volatile component with passage of time subsequent to the paint application is determined as shown in FIG. 10.

After the determination of the change in rate ΔT of evaporation of the volatile component, procedures described with reference to FIGS. 9(e) to 9(h) which are similar respectively to the procedures described with reference to FIGS. 4(a) to 4(e) are successively applied to another standard sample 2Pw of the same composition as the weighing sample 8Pw. Specifically, with respect to such another weighing sample 2Pw, an application of the painting material to a small piece 2, a measurement of the second intensity $I_{C2}$ of the Compton scattering rays, a drying, a weighing of a dried standard sample $2P_D$ and a weighing of a minute cut piece 2 are successively performed.

At this time, a length of time t passing subsequent to the paint application as shown in FIG. 9(e) to the measurement of the second intensity $I_{C2}$ of the Compton scattering rays Bc as shown in FIG. 9(f) is measured. Then, using the graph of FIG. 10, the rate ΔT of evaporation of the volatile component which takes place during the length of time t is determined. On the other hand, by subtracting the amount of the volatile component evaporated from the amount $W_{PW}$ of coating of the painting material on the standard sample 2Pw immediately after the paint application, the amount $W_{PW}(1-\Delta T)$ of coating of the painting material at the time of measurement of the second intensity $I_{C2}$ of the Compton scattering rays Bc is determined. Thereafter, a relationship between the second intensity $I_{C2}$ of the Compton scattering rays Bc and the amount $W_{PW}(1-\Delta T)$ of paint coating is determined with respect to a plurality of standard samples 2Pw having different amounts $W_{PW}$ of paint coating, to thereby give the calibration curves.

After the determination of the calibration curves, the measurement is carried out while the sample is transported along the painting line shown in FIG. 3 so that, using the above described calibration curve, the amount $W_{PW}$ of coating of the painting material in a wet condition on the sample 10A is determined. The method of determination thereof is similar to that described in connection with the second embodiment of the present invention shown in and described with reference to FIG. 2 and, therefore, the details thereof are not reiterated for the sake of brevity.

Thus, the measurement according to FIG. 9 is such that the rate ΔT of evaporation of the volatile component during a passage of time immediately after the paint application is first determined and, then, the calibration curve is determined on the basis of the second intensity $I_{C2}$ of the Compton scattering rays Bc, emitted from the standard sample 2Pw, and the amount $W_{PW}(1-\Delta T)$ of paint coating at the time of measurement of such second intensity $I_{C2}$. Therefore, no error which would result from the amount of the volatile component evaporated during the passage of time subsequent to the paint application and before the measurement of the second intensity $I_{C2}$ does not occur, ensuring an accurate measurement of the calibration curve. Hence, with the method of FIG. 9, the amount $W_{PW}$ of paint coating on the sample 10A to be analyzed can be accurately determined.

Figure 11:
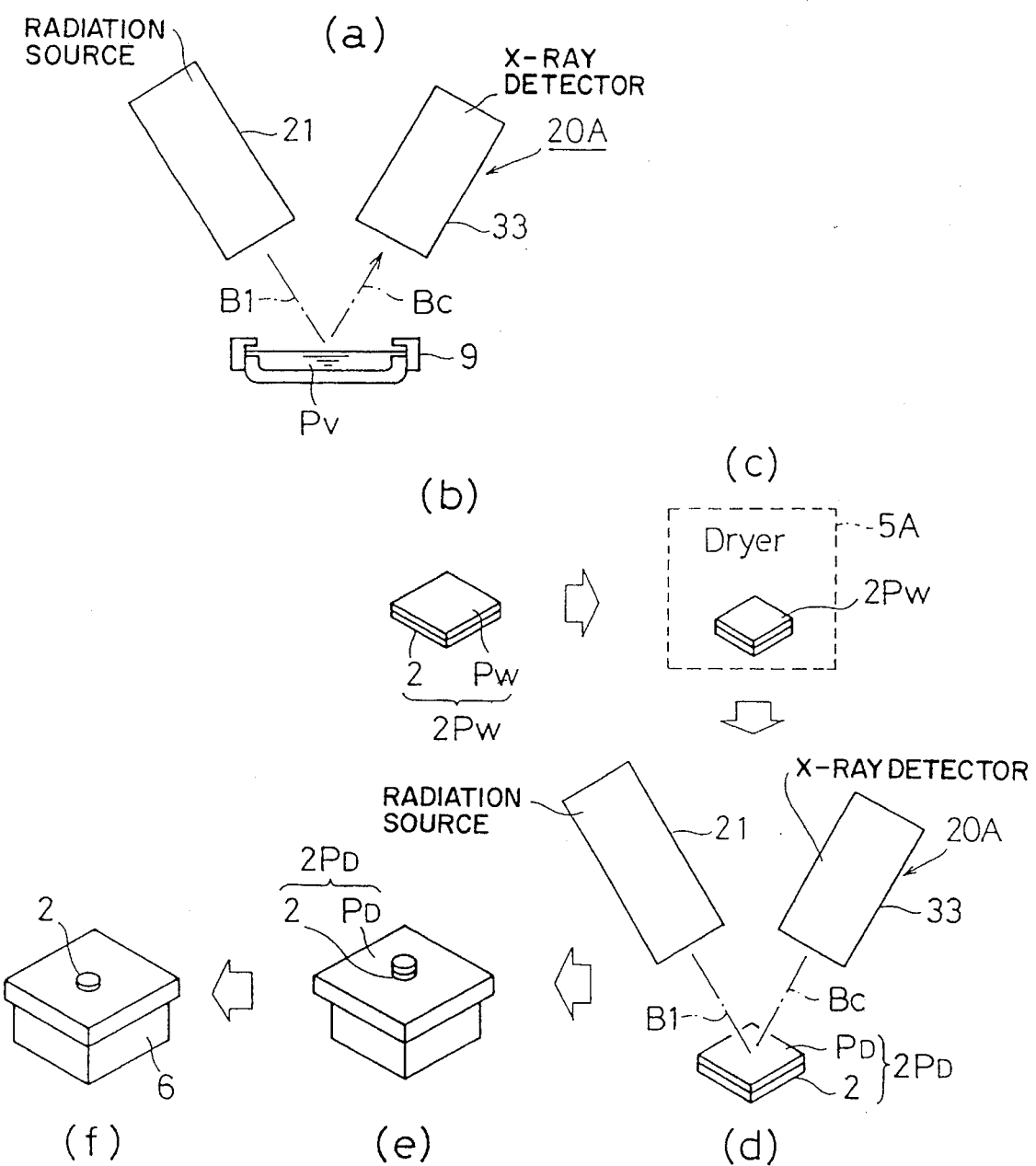
FIG. 11 is a schematic diagram showing the manner by which constants $\alpha_1$ and $\alpha_2$ of the calibration curve are determined.
Figure 12A:
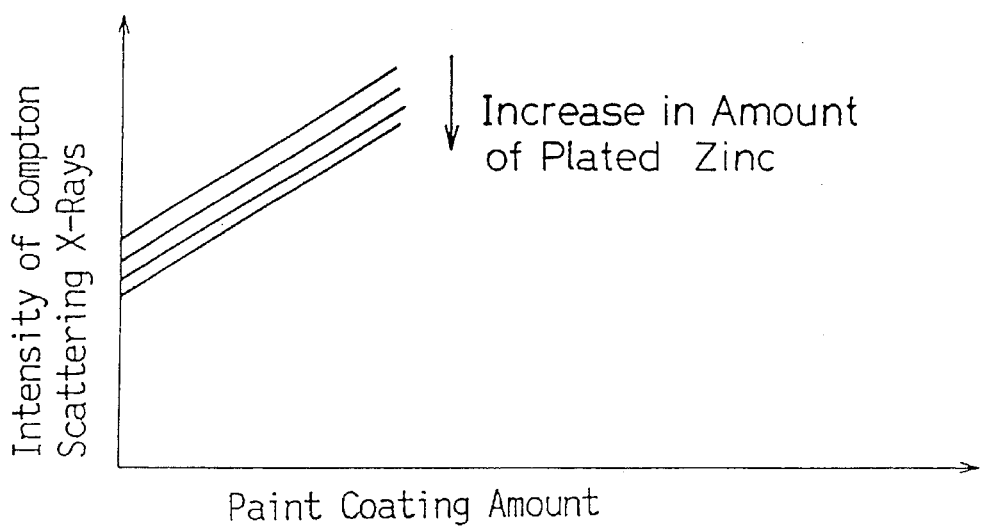
FIG. 12(a) is a chart showing a change in intensity of the Compton scattering rays in the case of a galvanized steel.
Figure 12B:
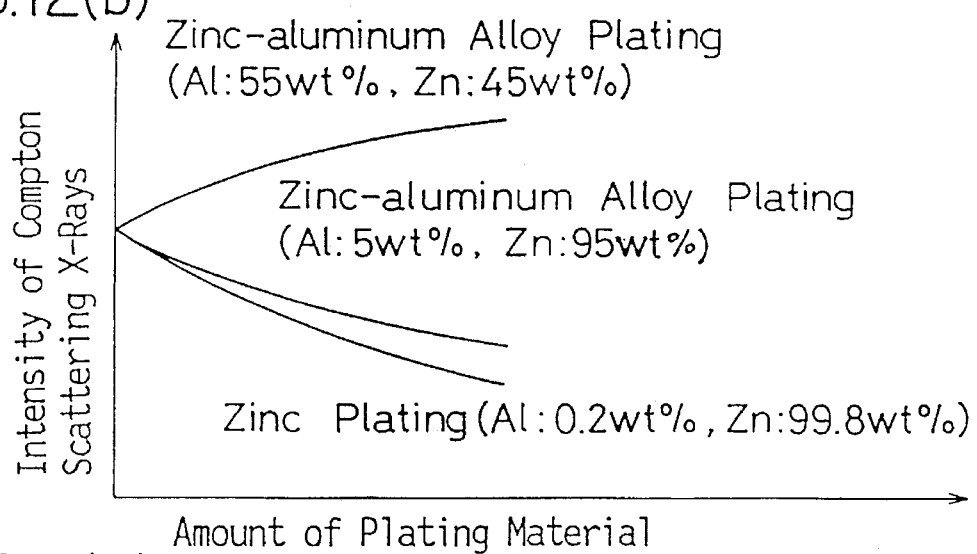
FIG. 12(b) is a chart showing how the intensity of the Compton scattering rays changes in dependence on the type of material for a substrate.
Figure 12C:
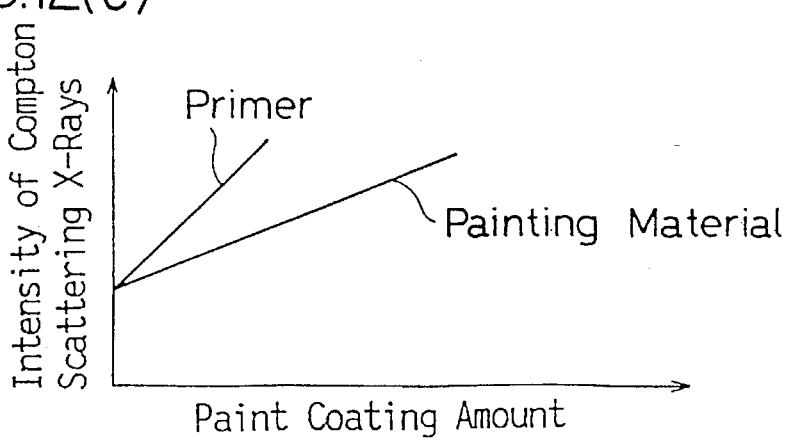
FIG. 12(c) is a chart showing how the intensity of the Compton scattering rays changes in dependence on the type of a painting material.

FIG. 11 illustrates a further preferred method of determination of the calibration curve according to the present invention.

As shown in FIG. 11(a), the volatile component Pv which is a solvent contained in the painting material is sealed within a container 9 so as to avoid any possible evaporation thereof. Thereafter, using the measuring apparatus 20A, the intensity Iv of the Compton scattering rays Bc scattered from the volatile component Pv is measured. This measurement is carried out subject to a plurality of volatile components Pv of varying depth to give respective constants $\alpha_1$ of calibration curve for the volatile components Pv. It is to be noted that, even though the composition of the pigments (non-volatile components) $P_D$ changes, the volatile component Pv does not change, and therefore, the calibration curve constant $\alpha_1$ is fixed.

On the other hand, as will be described with reference to FIGS. 11(b) to 11(f), another constant $\alpha_2$ of calibration curve for the non-volatile component $P_D$ is determined.

In order to determine the calibration curve constant $\alpha_2$, a paint material is applied to a small piece 2 to produce a standard sample 2Pw as shown in FIG. 11(b). This standard sample 2Pw is subsequently loaded into the drying unit 5A as shown in FIG. 11(c) to evaporate the volatile component thereby to give the dried standard sample $2P_D$ as shown in FIG. 11(d).

The dried standard sample $2P_D$ is then loaded into the measuring apparatus 20A to measure the intensity $I_D$ of the Compton scattering rays Bc scattered from the dried painted layer $P_D$. After this measurement, a minute portion of the standard sample 2Pw which has been irradiated with the radiations for the measurement of the intensity $I_D$ of the Compton scattering rays Bc scattered therefrom is cut out, followed by a measurement of the weight $W_{2D}$ of the small dried standard sample $2P_D$ as shown in FIG. 11(e). Subsequently, the painted layer $P_D$ is peeled off by the use of a chemical process and, then, as shown in FIG. 11(f), the weight $W_2$ of the small piece 2 is measured.

After this weighing, the weight $W_2$ of the cut piece 2 is subtracted from the weight $W_{2D}$ of the dried standard sample $2P_D$, followed by a division by the area a of surface of the minute small piece 2 to give the amount $T_D$ $(=W_{2D}-W_2)/\alpha$ of coating of the dried painted layer. Then, the amount $T_D$ of paint coating of the dried painted layer and the intensity $I_D$ of the Compton scattering rays Bc generated therefrom are measured with a plurality of the standard samples $2P_D$ and, by carrying out a recurrent calculation, the constant $\alpha_2$ of the calibration curve for the dried painted layer $P_D$, that is, for the non-volatile component $P_D$, is obtained.

The manner in which a constant α of the calibration curve used to determine the amount $W_{PW}$ of coating of the wet painted layer is determined in reference to the respective constants $\alpha_1$ and $\alpha_2$ of calibration curve for the volatile component Pv and the non-volatile component $P_D$ and the ratio K of the nonvolatile component relative to the volatile component will now be described.

The intensities Iv and $I_D$ of the Compton scattering rays Bc referred to hereinabove are expressed by the following equations (41) and (42), respectively:

$$Iv = A_{11}\{1-\exp(-B_{11}Tv)\} \qquad (41)$$

$$I_D = A_{12}\{1-\exp(-B_{12}T_D)\} \qquad (42)$$

wherein:

$A_{11}$ and $A_{12}$: Constants.

$B_{11}$: Coefficient of mass absorption of the radiation by the volatile component.

$B_{12}$: Coefficient of mass absorption of the radiation by the non-volatile component.

Tv: Amount of coating of the volatile component.

$T_D$: Amount of coating of the non-volatile component.

Since $B_{11}Tv \ll 1$ and $B_{12}T_D \ll 1$, the above equations (41) and (42) can be approximately modified into the following equations (51) and (52), respectively:

$$Iv = A_{11}B_{11}Tv \quad (51)$$

$$I_D = A_{12}B_{12}T_D \quad (52)$$

Assuming that $A_{11}B_{11} = 1/\alpha_1$ and $A_{12}B_{12} = 1/\alpha_2$, the above modified equations (51) and (52) can be expressed by the following equations (61) and (62), respectively:

$$Tv = \alpha_1 Iv \quad (61)$$

$$T_D = \alpha_2 I_D \quad (62)$$

On the other hand, the amount $W_{PW}$ of paint coating of the wet painted layer and the intensity Ic of the Compton scattering rays emitted therefrom can be expressed by the following equations (43) and (44), respectively:

$$W_{PW} = Tv + T_D \quad (43)$$

$$Ic = Iv + I_D \quad (44)$$

Also, the ratio K of the non-volatile component has the following relationship:

$$T_D = KW_{PW} \quad (45)$$

Again, the amount $W_{PW}$ of paint coating and the intensity Ic of the Compton scattering rays Bc emitted therefrom have the following relationship:

$$W_{PW} = \alpha Ic \quad (46)$$

Solving the foregoing equations (61), (62), (43), (44), (45) and (46) results in the following equation (47) which gives the constant $\alpha$ of the calibration curve to be used in the quantitative determination of the amount $W_{PW}$ of paint coating forming the wet painted layer.

$$\alpha = \alpha_1\alpha_2/\{\alpha_2(1-K) + \alpha_1 K\} \quad (47)$$

Using the calibration curve constant $\alpha$ determined in the manner described above and the first intensity Ic of the Compton scattering rays Bc measured while the sample is transported along the painting line shown in FIG. 3, the amount $W_{PW}$ of paint coating is calculated according to the foregoing equation (46). It is to be noted that the calibration curve constant $\alpha$ corresponds to the parameter $A_1B_1$ in the equation (31) and is expressed by $\alpha = 1/(A_1 \cdot B_1)$.

Thus, according to the last mentioned preferred method of determination of the calibration curve, the calibration curve constant $\alpha$ to be used for the determination of the amount $W_{PW}$ of paint coating forming the wet painted layer is determined in dependence on the respective constants $\alpha_1$ and $\alpha_2$ of calibration curve for the volatile component Pv and the non-volatile component $P_D$ and the ratio K of the non-volatile component. Therefore, any possible error which would result from an evaporation of the volatile component Pv can be eliminated, ensuring an improved accuracy of analysis.

It has been found that, when using the calibration curve constant $\alpha$ the amount $W_{PW}$ of paint coating was measured, a measurement error could be reduced down to 0.6 g/m$^2$ as compared with the measurement error of 3 to 4 g/m$^2$ exhibited by the method shown in and described with reference to FIG. 4, where the amount $W_{PW}$ is 20 g/m$^2$.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. By way of example, in the practice of the present invention, the amount $W_{PW}$ of paint coating forming the wet painted layer may be determined using the calibration curve determined according to the method shown in any one of FIGS. 7 to 11, not according to the generalized method shown in and described with reference to FIG. 4.

Also, any one of the first and second embodiments shown in and described with reference to FIGS. 1 and 2, respectively, may be utilized to determine not only the amount $W_{PW}$ of paint coating of the wet painted layer, but also the amount of paint coating of the dry painted layer.

Accordingly, such changes and modifications are, unless they depart from the scope of the present invention as delivered from the claims annexed hereto, to be construed as included therein.

What is claimed is:

1. A method of measuring the amount of coating of a painting material on a galvanized substrate, which comprises the steps of:

directing any one of X-rays and Gamma-rays onto a surface of a sample including the substrate and the painted layer thereon;

measuring simultaneously an intensity of Compton scattering rays emitted from an irradiated portion of the sample and an intensity of fluorescent X-rays emitted from the irradiated portion within the substrate of the sample, each time measurement of the amount of the deposited painting material is carried out;

describing the measured intensity of the Compton scattering rays by a first function having variables represented by an amount of the galvanizing material and the amount of the deposited painting material, respectively, said first function including absorption components associated with said amount of the galvanizing material and said amount of the painting material;

describing the measured intensity of the fluorescent X-rays by a second function having variables represented by the amount of the galvanizing material and the amount of the deposited painting material, respectively, said second function including absorption components associated with said amount of the galvanizing material and said amount of the painting material;

solving simultaneously the first and second functions to thereby determine the amount of the deposited painting material.

2. The method of measuring the amount of coating of a painting material as claimed in claim 1, further comprising the steps of:

measuring a weight of a cut piece cut from the substrate before the painting material is applied;

applying a painting material of a composition identical with that of the painting material applied to the substrate to provide a standard sample;

measuring a weight of the standard sample in a wet condition and simultaneously directing radiation onto the standard sample;

measuring an intensity of Compton scattering rays emitted from the standard sample;

determining an amount of coating of the painting material on the standard sample in the wet condition in reference to the measured weight of the standard sample before the painting material is applied and that measured during the directing of the radiation; and determining a calibration curve for the intensity of the Compton scattering rays based on the amount of coating of the painting material on the standard sample in the wet condition and the intensity of the Compton scattering rays emitted from the sample, wherein said calculating step is carried out with the use of said calibration curve to determine the amount of coating of the painting material forming the outer painted layer.

3. The method of measuring the amount of coating of a painting material as claimed in claim 1, further comprising the steps of:

determining a change in amount of a volatile component of the painting material forming the outer painted layer with passage of time;

applying a painting material of a composition identical with that of the painting material used to form the outer painted layer, to a cut piece cut from the substrate thereby to provide a standard sample;

directing radiation onto the standard sample so as to measure an intensity of Compton scattering rays emitted from the standard sample;

determining the amount of the volatile component which has been evaporated in reference to a length of time passed immediately after the application of the painting material to the cut piece and by the time the intensity of the Compton scattering rays emitted form the standard sample is measured and also in reference to the change in amount of the volatile component with passage of time;

determining the amount of coating of the painting material on the standard sample at the time of directing the radiation by subtracting the amount of the volatile component evaporated from the amount of coating of the painting material immediately after the painting material has been applied to the cut piece to form the standard sample; and determining a calibration curve for the intensity of the Compton scattering rays based on the amount of coating of the painting material on the standard sample at the time of the radiation and the intensity of the Compton scattering rays emitted from the sample, wherein said calculating step is carried out with the use of said calibration curve to determine the amount of coating of the painting material forming the outer painted layer.

4. The method of measuring the amount of coating of a painting material as claimed in claim 1, further comprising the steps of:

determining a first constant $\alpha 1$ of calibration curve representative of a volatile component contained in the painting material forming the outer painted layer;

determining a second constant $\alpha 2$ of calibration curve representative of a non-volatile component of the painting material obtained by measuring a component contained in the painting material forming the outer painted layer after drying; and determining a constant $\alpha$ of calibration curve for the intensity of the Compton scattering rays on the basis of a proportion K of the non-volatile component remaining in the painting material forming the outer painted layer, said first and second constants $\alpha 1$ and $\alpha 2$, wherein said calculating step is carried out with the use of said calibration curve $\alpha$ constant to determine the amount of the painting material forming the outer painted layer.

5. An apparatus for measuring the amount of coating of a painting material forming a painted layer on a galvanized substrate, comprising:

a source of radiation, including any one of X-rays and Gamma-rays, to be directed onto a surface of the painted layer on a sample comprising a substrate having the painted layer formed thereon;

first analyzing means for measuring an intensity of Compton scattering rays emitted from an irradiated portion of the sample;

second analyzing means for measuring an intensity of fluorescent X-rays emitted from the irradiated portion within the substrate simultaneously with measurement of the intensity of the Compton scattering rays, each time measurement of the deposited painting material is carried out; and arithmetic means for describing the measured intensity of the Compton scattering rays by a first function having variables represented by an amount of the galvanizing material and the amount of the deposited painting material, respectively, said first function including absorption components associated with said amount of the galvanizing material and said amount of the painting material, and also for describing the measured intensity of the fluorescent X-rays by a second function having variables represented by the amount of the galvanizing material and the amount of the deposited painting material, respectively, said second function including absorption components associated with said amount of the galvanizing material and said amount of the painting material, and also for describing the measured intensity of the fluorescent X-rays by a second function having variables represented by the amount of the galvanizing material and the amount of the deposited painting material, respectively, said second function including absorption components associated with said amount of the galvanizing material and said amount of the deposited painting material, said arithmetic means being also operable for simultaneously solving the first and second functions to thereby determine the amount of the deposited painting material.

6. A method of measuring the amount of coating of a painting material forming outer and inner painted layers on a galvanized substrate, which comprises the steps of:

directing radiation, including any one of X-rays and Gamma-rays, onto a surface of a sample including the substrate having the outer and inner painted layers formed thereon;

measuring simultaneously an intensity of Compton scattering rays emitted from an irradiated portion of the sample, an intensity of first fluorescent X-rays emitted from the irradiated portion within the substrate and an intensity of second fluorescent X-rays emitted from the irradiated portion within the inner painted layer, each time measurement of the amount of the painting material is carried out;

describing the measured intensity of the Compton scattering rays by a first function having variables represented by an amount of the galvanizing material, an amount of the deposited first painting material forming the inner painted layer, and an amount of the deposited second painting material forming the outer painted layer, respectively, said first function including absorption components associated with said amount of the galvanizing material, said amount of the first deposited painting material and said amount of the deposited second painting material;

describing the measured intensity of the first fluorescent X-rays by a second function having variables represented by the amount of the galvanizing material, the amount of the deposited first painting material, and the amount of the deposited second painting material, respectively, said second function including absorption components associated with said amount of the galvanizing material, said amount of the deposited first painting material and said amount of the deposited second painting material;

describing the measured intensity of the second fluorescent X-rays by a third function having variables represented by the amount of the deposited first painting material and the amount of the deposited second painting material, respectively, said third function including absorption components associated with said amount of the deposited first painting material and said amount of the deposited second painting material; and solving simultaneously the first, second and third functions to thereby determine the amount of the deposited second painting material of the outer painted layer.

7. The method of measuring the amount of coating of a painting material as claimed in claim 6, wherein said sample comprises the substrate continued in a moving direction and having the inner painted layer and the outer painted layer which is in a wet condition.

8. The method of measuring the amount of coating of a painting material as claimed in claim 6, further comprising the steps of:

measuring a weight of a cut piece cut from the substrate before the painting material is applied;

applying a painting material of a composition identical with that of the painting material applied to the substrate to provide a standard sample;

measuring a weight of the standard sample in a wet condition and simultaneously directing radiation onto the standard sample;

measuring an intensity of Compton scattering rays emitted from the standard sample;

determining an amount of coating of the painting material on the standard sample in the wet condition in reference to the measured weight of the standard sample before the painting material is applied and that measured during the directing of the radiation; and determining a calibration curve for the intensity of the Compton scattering rays based on the amount of coating of the painting material on the standard sample in the wet condition and the intensity of the Compton scattering rays emitted from the sample, wherein said calculating step is carried out with the use of said calibration curve to determine the amount of coating of the painting material forming the outer painted layer.

9. The method of measuring the amount of coating of a painting material as claimed in claim 6, further comprising the steps of:

determining a change in amount of a volatile component of the painting material forming the outer painted layer with passage of time;

applying a painting material of a composition identical with that of the painting material used to form the outer painted layer, to a cut piece cut from the substrate thereby to provide a standard sample;

directing radiation onto the standard sample so as to measure an intensity of Compton scattering rays emitted from the standard sample;

determining the amount of the volatile component which has been evaporated in reference to a length of time passed immediately after the application of the painting material to the cut piece and by the time the intensity of the Compton scattering rays emitted from the standard sample is measured and also in reference to the change in amount of the volatile component with passage of time;

determining the amount of coating of the painting material on the standard sample at the time of directing the radiation by subtracting the amount of the volatile component evaporated from the amount of coating of the painting material immediately after the painting material has been applied to the cut piece to form the standard sample; and determining a calibration curve for the intensity of the Compton scattering rays based on the amount of coating of the painting material on the standard sample at the time of the radiation and the intensity of the Compton scattering rays emitted from the sample, wherein said calculating step is carried out with the use of said calibration curve to determine the amount of coating of the painting material forming the outer painted layer.

10. The method of measuring the amount of coating of a painting material as claimed in claim 6, further comprising the steps of:

determining a first constant $\alpha 1$ of calibration curve representative of a volatile component contained in the painting material forming the outer painted layer;

determining a second constant $\alpha 2$ of calibration curve representative of a non-volatile component of the painting material obtained by measuring a component contained in the painting material forming the outer painted layer after drying; and determining a constant $\alpha$ of calibration curve for the intensity of the Compton scattering rays on the basis of a proportion K of the non-volatile component remaining in the painting material forming the outer painted layer, said first and second constants $\alpha 1$ and $\alpha 2$, wherein said calculating step is carried out with the use of said calibration curve $\alpha$ constant to determine the amount of the painting material forming the outer painted layer.

11. An apparatus for measuring the amount of coating of a painting material forming outer and inner painted layers on a galvanized substrate, comprising:

a source of radiation, including any one of X-rays and Gamma-rays, to be irradiated onto a surface of a sample comprising the substrate having the outer and inner painted layers thereon;

first analyzing means for measuring an intensity of Compton scattering rays emitted from an irradiated potation of the sample;

second analyzing means for measuring an intensity of first fluorescent X-rays emitted from the irradiated portion within the substrate simultaneously with measurement of the intensity of the Compton scattering rays, each time measurement of the deposited painting material is carried out;

third analyzing means for measuring an intensity of second fluorescent X-rays emitted from the irradiated portion within the inner painted layer simultaneously with measurement of the intensity of the Compton scattering rays, each time measurement of the amount of the painting material is carried out; and arithmetic means for describing the measured intensity of the Compton scattering rays by a first function having variables represented by an amount of the galvanizing material, an amount of the deposited first painting material forming the inner painted layer, and an amount of the deposited second painting material forming the outer painted layer, respectively, said first function including absorption components associated with said amount of the galvanizing material, said amount of the deposited first painting material and said amount of the deposited second painting material, also for describing the measured intensity of the first fluorescent X-rays by a second function having variables represented by the amount of the galvanizing material, the amount of the deposited first painting material, and the amount of the deposited second painting material, respectively, said second function including absorption components associated with said amount of the galvanizing material, said amount of the deposited first painting material and said amount of the deposited second painting material, and further for describing the measured intensity of the second fluorescent X-rays by a third function having variables represented by the amount of the deposited first painting material and the amount of the deposited second painting material, respectively, said third function including absorption components associated with said amount of the deposited first painting material and said amount of the deposited second painting material, said arithmetic means being operable for simultaneously solving the first, second and third functions to thereby determine the amount of the deposited painting material of the outer painted layer.

* * * * *